United States Patent [19]

Yamatsuta et al.

[11] Patent Number: 4,653,106
[45] Date of Patent: Mar. 24, 1987

[54] INDENTATION HARDNESS METER

[75] Inventors: Sadao Yamatsuta; Fukumoto Mitoshi, both of Tokyo, Japan

[73] Assignee: Matsuzawa Seiki Kabushikikaisha, Tokyo, Japan

[21] Appl. No.: 618,392

[22] PCT Filed: Sep. 26, 1983

[86] PCT No.: PCT/JP83/00317

§ 371 Date: May 23, 1984

§ 102(e) Date: May 23, 1984

[87] PCT Pub. No.: WO84/01219

PCT Pub. Date: Mar. 29, 1984

[30] Foreign Application Priority Data

Sep. 25, 1982 [JP] Japan .................................. 57-166962
Sep. 26, 1983 [JP] Japan .................................. 58-1777783

[51] Int. Cl.[4] .......................... G06K 9/00; G01N 3/48
[52] U.S. Cl. ........................................... 382/8; 73/81;
358/101; 358/107; 356/378; 356/379
[58] Field of Search .................... 73/81; 356/378–381,
356/383, 384, 387; 358/101, 107; 382/8, 65

[56] References Cited

U.S. PATENT DOCUMENTS

| 3,754,436 | 8/1973 | Saxton | 73/81 |
|---|---|---|---|
| 3,848,089 | 11/1974 | Stewart | 382/65 |
| 4,147,052 | 4/1979 | Tsujiuchi et al. | 356/378 |
| 4,149,187 | 4/1979 | Palmer | 358/107 |
| 4,222,262 | 9/1980 | Batie et al. | 73/81 |
| 4,255,966 | 3/1981 | Batie et al. | 73/81 |
| 4,277,174 | 7/1981 | Kleesattel | 356/378 |
| 4,354,761 | 10/1982 | Jacoby | 356/378 |
| 4,435,837 | 3/1984 | Abernathy | 356/380 |
| 4,463,600 | 8/1984 | Hobbs et al. | 73/81 |

Primary Examiner—Leo H. Boudreau
Attorney, Agent, or Firm—Gerald J. Ferguson, Jr.; Michael P. Hoffman; Ronni S. Malamud

[57] ABSTRACT

An impression made in a specimen is imaged by a one-dimensional scanning image sensing device, and in the case of the impression being quadrangular pyramidal, a signal representing the length of its diagonal are generated from the image output, and in the case of the impression being spherical, a signal representing its diameter is generated from the image output. The scanning by the one-dimensional scanning image sensing device does not cover the area of the impression over the entire width thereof but instead the scanning is effected for a first region of a small width which, in the case of the impression being quadrangular pyramidal, contains its first diagonal and, in the case of the impression being sperical, contains its diameter in a first direction. Next, when the impression is quadrangular pyramidal, the scanning is performed for a second of a small width which contains a second diagonal of the impression, or third and fourth regions which contains two vertexes of the second diagonal of the impression and is parallel to the first region.

3 Claims, 14 Drawing Figures

INDENTATION HARDNESS METER

TECHNICAL FIELD

The present invention relates to an indentation hardness meter which impresses an indenter into a specimen of a metallic material or the like to make therein a quadrangular pyramidal or spherical impression and measures the hardness of the specimen by measuring the lengths of first and second diagonals of the quadrangular pyramidal impression or diameter of the spherical impression.

BACKGROUND ART

As the abovesaid type of indentation hardness meter, there has heretofore been proposed such an arrangement in which a quadrangular pyramidal impression made in a specimen is imaged by scanning through the use of a scanning image sensing device, first and second diagonal-length signals representing the lengths of first and second diagonals of the impression are obtained from the image output and a hardness signal representing the hardness of the specimen is derived from the first and second diagonal-length signals.

The conventional indentation hardness meter of such an arrangement possesses, however, defects that a complex, bulky and expensive scanning image sensing device is needed which is capable of imaging the impression by scanning its entire area two-dimesionally, that the arrangement for obtaining the first and second diagonal-length signals from the image output of the scanning image sensing device is extremely complex and that a relatively long period of time is required for obtaining the first and second diagonal-length signals.

DISCLOSURE OF THE INVENTION

According to the present invention, an indentation made in a specimen is imaged by scanning through a one-dimensional scanning image sensing device and, in the case of the indentation being quadrangular pyramidal, signals representing the lengths of its diagonals are produced and, in the case of the indentation being spherical, a signal representing its diameter is generated.

The scanning by the one-dimensional scanning image sensing device in this case does not cover the entire area of the impression but covers its area of a smaller width which contains its diagonals in the case of the impression being quadrangular pyramidal and its diameter in the case of the impression being spherical.

Therefore, the present invention is free from the abovesaid defects of the prior art.

BEST MODE FOR CARRYING OUT THE INVENTION

Embodiment 1

A description will be given first of a first embodiment of the indentation hardness meter of the present invention.

Figure 1:
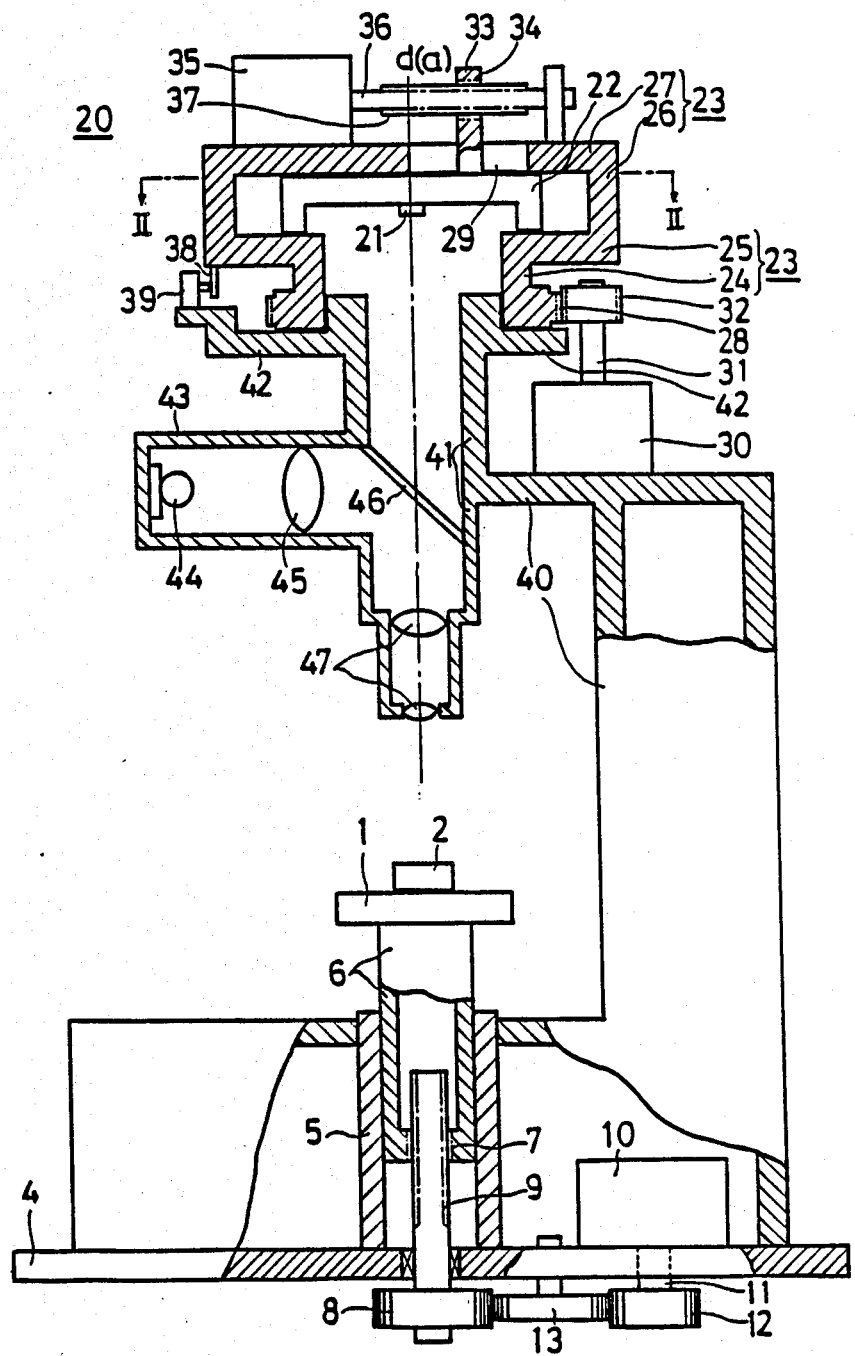
FIG. 1 is a schematic sectional view illustrating an example of the mechanical system of a first embodiment of the indentation hardness meter of the present invention.
Figure 2:
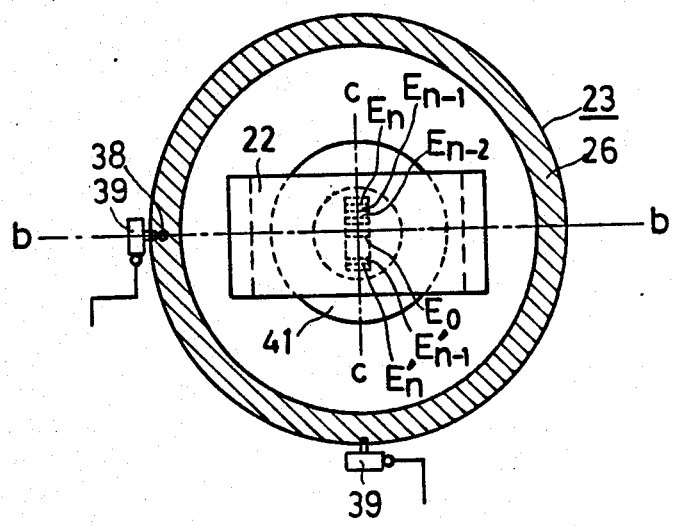
FIG. 2 is a sectional view taken on the line II—II in FIG. 1.

FIGS. 1 and 2 illustrate an example of the mechanical arrangement of the indentation hardness meter of the present invention, which is provided with a vertically movable specimen table 1.

Figure 3:
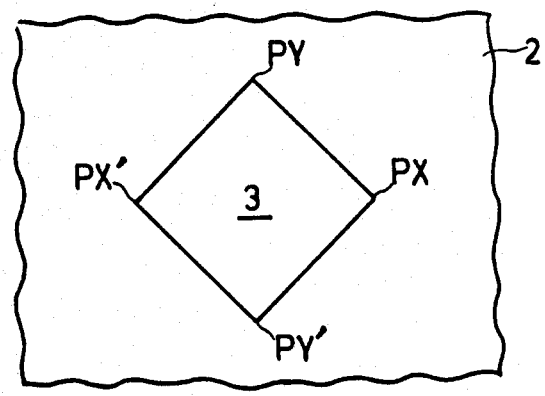
FIG. 3 is a diagram showing an indentation made in a specimen.

As in an ordinary indentation hardness meter, the specimen table 1 holds thereon a specimen 2 for impression thereinto an indenter (not shown) to make therein such a quadrangular pyramidal indentation 3 as shown in FIG. 3, and this specimen table has such a structure as described below.

That is, a tubular member 5 is fixedly mounted on a base 4, and another tubular member 6 carrying at its free end the abovesaid specimen table 1 is received in the tubular member 5 in a manner to be movable up and down. In this case, the inner peripheral surface of the inner end of the tubular member 6 has cut therein screw threads 7.

On the other hand, a threaded shaft 9, which threadedly engages the female screw 7 of the abovesaid tubular member 6 and carries at the free end a gear 8, is pivotally secured to the base 4.

Further, a motor 10 is mounted on the base 4, and its rotary shaft 11 is connected to the threaded shaft 9 through a gear 12 affixed to the rotary shaft, a gear 13 pivotally secured to the base 4 and the abovesaid gear 8 mounted on the threaded shaft 9.

Accordingly, when the motor 10 is driven to rotate in the forward direction, the threaded shaft 9 is rotated in the forward direction to raise the tubular member 6, and consequently the specimen table 1 moves up.

When the motor 10 is driven in the reverse direction, the threaded shaft 9 rotates in the reverse direction to lower the tubular member 6, and consequently, the specimen table 1 moves down.

Moreover, the illustrated example of the mechanical system of the first embodiment of the indentation hardness meter of the present invention has a image sensing device mount 20.

The image sensing device mount 20 has a movable board 22 having mounted thereon a one-dimensional scanning image sensing device 21 and a holder 23 which movably supports the movable board 22.

The holder 23 comprises a tubular portion 24, an annular portion 25 which is formed integrally with its upper end portion to extend therefrom outwardly in the radial direction, a tubular portion 26 which is formed integrally with the outer marginal portion of the annular portion 25 to extend therefrom upwardly, and a plate portion 27 which is formed integrally with the upper end portion of the tubular portion 26 to extend therefrom inwardly in the radial direction. In this case, a gear 28 is provided on the outer peripheral surface of the tubular portion 24. Further, the plate portion 27 has made therein a slit 29.

Such a holder 23 is rotatably mounted on a tubular member 41, with its tubular portion 24 loosely receiving the upper end portion of the tubular member 41 and the lower end face of the tubular portion 24 resting on an annular plate 42 which is formed integrally with the outer peripheral portion of the tubular member 41 to extend therefrom outwardly in the radial direction.

On the other hand, a support 40 is fixedly mounted on the aforesaid base 4, and a motor 30 is mounted on the support 40.

Further, a rotary shaft 31 of the motor 30 is connected to the holder 23 through a gear 32 mounted on the rotary shaft and the abovesaid gear 28 provided on the tubular portion 24 of the holder 23.

Accordingly, when the motor 30 is driven to rotate in the forward direction, the holder 23 is rotated in the forward diection, and when the motor 30 is driven in the reverse direction, the holder 23 rotates in the reverse direction.

The aforementioned movable board 22 is disposed between the annular portion 25 and the plate portion 27 of the holder 23 in a manner to be movable along a line b—b which passes through the axis a of the holder 23 and intersects it at right angles thereto.

Further, the movable board 22 has a rod 33 formed integrally therewith to extend upwardly thereof.

The rod 33 extends upwardly through the slit 29 made in the plate portion 27 of the holder 23.

Furthermore the free end of the rod 33 has cut therein a female screw 34 which extends on a line parallel to the line b—b in a plane intersecting the axis a of the holder 23.

On the other hand, a motor 35 is mounted on the plate portion 27 of the holder 23, and its rotary shaft 36 has cut screw threads 37 for threaded engagement with the female screw 34 of the rod 33.

Accordingly, when the motor 35 is driven to rotate in the forward direction, the movable board 22 moves in a first direction along the line b—b perpendicular to the axis a of the holder 23, and when the motor 35 is driven in the reverse direction, the movable board 22 moves along the line b—b perpendicular to the axis a of the holder 23 in a second direction reverse from the first direction.

Furthermore the aforementioned one-dimensional scanning image sensing device 21 has such an arrangement that many ($2_{n+1}$) solid-state image sensors (photoelectric transducers) $E_n'$, $E_{n-1}'$, ... $E_1'$, $E_0$· $E_1$· $E_2$· ... $E_n$ are electrically connected in series one after another and are one-dimensionally aligned in a line, as will be evident from FIG. 5.

Such a one-dimensional scanning image sensing device 21 is mounted on the underside of the movable board 22 so that the line of arrangement on which the solid-state image sensors $E_n'$ to $E_1'$, $E_{0'}$ $E_1$ to $E_n$ are aligned extends across the axis a of the holder 23 and agree with a line c—c perpendicular to the line b—b, as viewed from the direction along the axis a of the holder 23.

Further, the annular portion 25 of the holder 23 has planted thereon an engaging pin 38 which extends downwardly thereof.

On the other hand, there are mounted on the aforementioned annular plate 42 switches 39 and 39' which are activated when engaged with the engaging pin 38 planted on the holder 23. These switches 39 and 39' are spaced apart an angular distance of 90° relative to the axis a of the holder 23.

Moreover, the aforesaid tubular member 41 is secured to a support 40 mounted on the base 4.

The tubular member 41 is mounted on the support 40 so that its axis d extends in the direction of vertical movement of the specimen table 1 and its one end bear a face-to-face relation to the specimen table 1.

Besides, the tubular member 41 has the annular plate 42 which is formed integrally therewith to extend outwardly in the radial direction thereof.

The tubular member 41 and the annular plate 42 rotatably support the holder 23, with the tubular member 24 receiving the tubular member 41 and the lower end face of the tubular member 24 of the holder 23 resting on the annular plate 42.

Accordingly, the axis a of the holder 23 is in agreement with the axis d of the tubular member 41.

Furthermore, the tubular member 41 has on one side thereof a tubular member 43 communicating therewith, and a light source 44 is disposed in the tubular member 43.

Light from the light source 44 is directed to the specimen 2 placed on the specimen table 1 through a lens 45 provided in the tubular member 42, half-mirror 46 provided in the tubular member 41 and a lens 47 provided in the tubular member 41, and the reflected light is directed to the one-dimensional scanning image sensing device 21 through the lens 47 and the half-mirror 46.

The foregoing has clarified an example of the mechanical system of the first embodiment of the indentation hardness meter of the present invention.

Next, a description will be given, with reference to FIG. 5, an example of the electrical system of the first embodiment of the indentation hardness meter of the present invention and its operation.

By applying the light from the light source 44 via the lens 45, the half-mirror 46 and the lens 47 to the specimen 2 and by applying the reflected light therefrom to the one-dimensional scanning image sensing device 21 via the lens 47 and the half-mirror 46, as described above, an image output (hereinafter identified generally by S) obtained by one-dimensional scanning of the specimen is provided from the one-dimensional scanning image sensing device 21.

Figure 4:
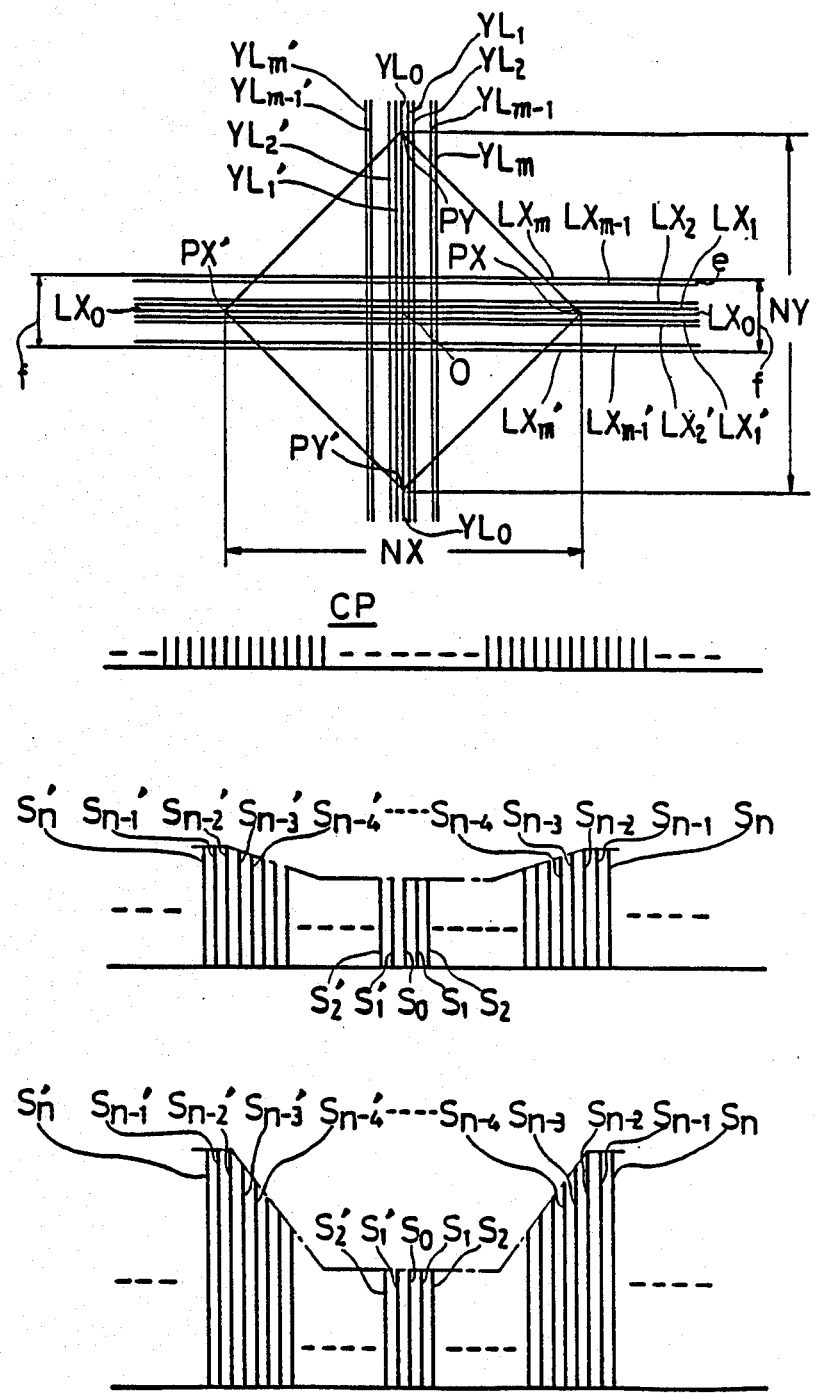
FIG. 4 is a diagram explanatory of imaging of the specimen by one-dimensional scanning through a one-dimensional image sensing device; and includes waveform diagrams explanatory of one-dimensional scanning of the specimen.
Figure 5:
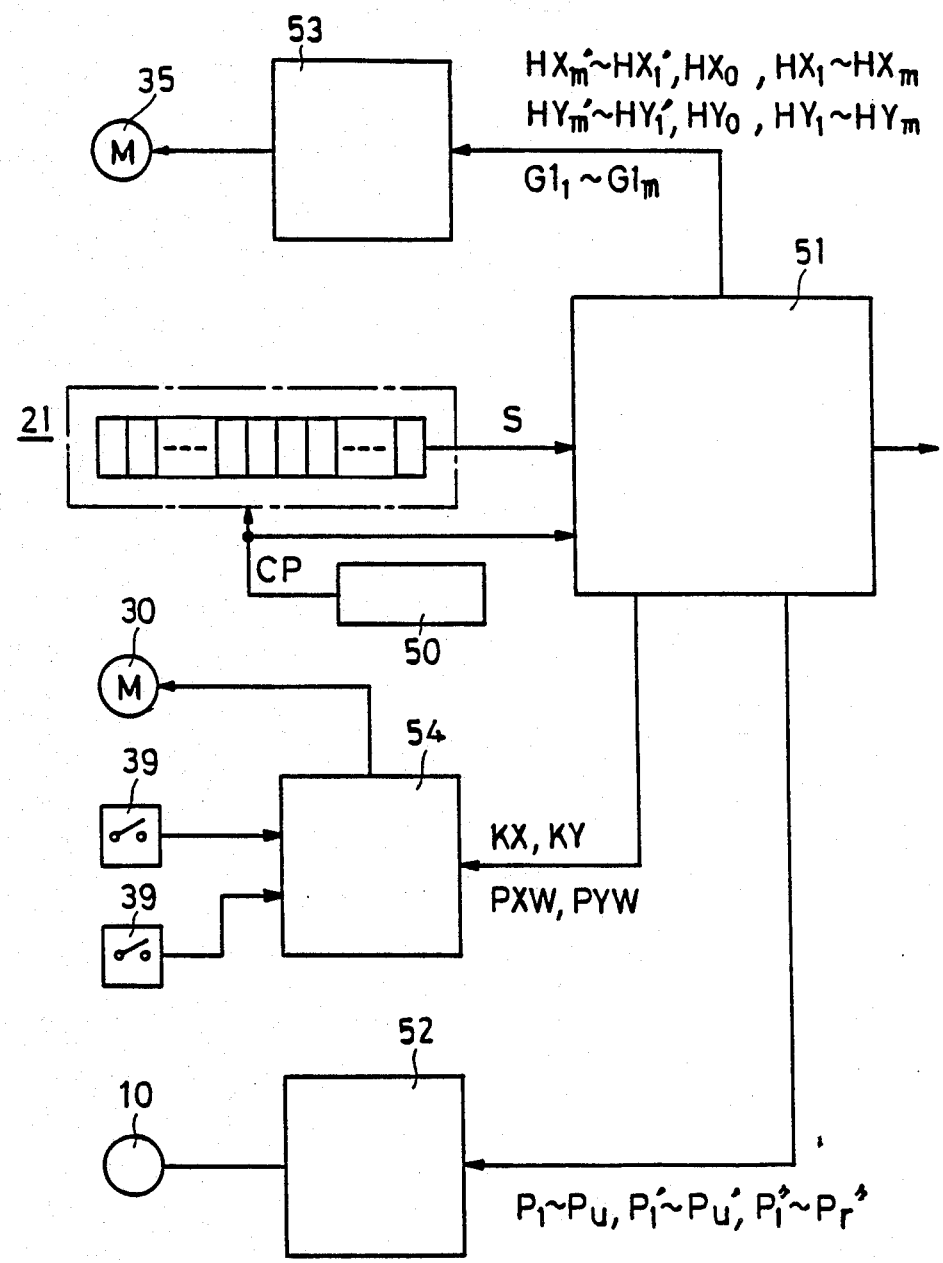
FIG. 5 is a systematic connection diagram illustrating an example of the electrical system of the first embodiment of the indentation hardness meter of the present invention in the case of using the mechanical system show in FIGS. 1 and 2.

In this case, as shown in FIG. 5, the one-dimensional scanning image sensing device 21 is driven under the control of clock pulses CP from a clock pulse generator 50, such as depicted in FIG. 4B.

Incidentally, the one-dimensional scanning image sensing device 21 has such as arrangement that the many solid-state image sensors $E_n'$, $E_{(n-1)}'$, ... $E_1'$, $E_{0'}$ $E_{1'}$ $E_{2'}$ ... $E_n$ are electrically connected in series one after another and one-dimensionally aligned in a line on the aforesaid line c—c, as referred to previously.

Accordingly, the image output S is obtained as photoelectric conversion outputs $S_n'$, $S_{(n-1)}'$, ... $S_1'$, $S_0$, $S_1$ $S_2$ ... $S_n$ which are sequentially provided, by the respective scanning of the one-dimensional scanning image sensing device 21, from the solid-state image sensors $E_n'$, $E_{(n-1)}'$, ... $E_1'$, $E_0$ $E_1$ $E_2$ ... $E_n$ respectively.

Now, let a line, which extends in a plane containing the surface of the specimen 2 and contains a diagonal joining a pair of opposing points PX and PX' of the impression 3 made in the specimen 2 on the specimen table 1 as shown in FIG. 3 (which diagonal will hereinafter be referred to as a first diagonal), be represented by $LX_0$ as shown in FIG. 4A, and let a line, which contains a diagonal joining the other pair of opposing points PY and PY' (which diagonal will hereinafter be referred to as a second diagonal), be represented by $LY_0$. Further, let an intersecting point of the lines $LX_0$ and $LY_0$ be represented by 0. Let a plurality m of lines, which extend in the plane containing the surface of the specimen 2 and in parallel to the line $LX_0$ and which are sequentially arranged at equal intervals e in a direction perpendicular to the line $LX_0$ on the side of the point PY with respect thereto over a range which is equal to one half of a width f smaller than the lengths of the abovesaid first and second diagonals (identified by NX and NY, respectively), that is, equal to f/2, be represented by $LX_1$, $LX_2'$ ... $LX_m'$ respectively, as shown in FIG. 4A. Let a plurality m of lines, which are sequentially arranged in parallel to the line $LX_0$ and at equal intervals e in the direction perpendicular to the line $LX_0$ on the side of the point PY' with respect thereto over the range equal to the abovesaid width f/2, be represented by $LX_1$, $LX_2'$, ... $LX_m'$, respectively.

Similarly, let a plurality m of lines, which are sequentially arranged in parallel to the line $LY_0$ and at equal intervals e in a direction perpendicular to the line $LY_0$ on the side of the point PX with respect thereto over a range equal to the abovesaid width f/2, be represented by $LY_1$, $LY_2$, ... $LY_m$, respectively. Further, let a plurality of lines, which are sequentially arranged in parallel to the line $LY_0$ and at equal intervals e in the direction perpendicular to the line $LY_0$ on the side of the point PX' with respect thereto over a range equal to the abovesaid width f/2, be represented by $LY_1'$, $LY_2'$, ... $LY_m'$, respectively.

Now, let it be assumed that the holder 23 having mounted thereon the one-dimensional scanning image sensing device 21 assumes its rotational position (which will hereinafter be referred to as a first rotational position), with the engaging pin 38 held in engagement with the switch 39 mounted on the annular plate 42, as shown in FIG. 2, and that the specimen 2 is preadjusted in position on the specimen table 1 so that the aforementioned line of arrangement c—c of the solid-state image sensors $E_n'$ to $E_1'$ $E_0$ and $E_1$ to $E_n$ of the one-dimensional scanning image sensing device 21 is parallel to and substantially in agreement with the abovesaid line $LX_0$ on the specimen 2 placed on the specimen table 1, as viewed from the direction along the axis a of the holder 23 and consequently along the axis d of the tubular member 41.

Further, let it be assumed that the holder 23 and the specimen table 1 each lie at such a position relative to the other that is lower than a relative position where the one-dimensional image sensing device 21 performs one-dimensional scanning of the impression 3 of the specimen 2 with its image held in focus (The former relative position will hereinafter be referred to as the in-focus position and the latter relative position as the reference position.).

In such a case, the outputs $S_n'$ to $S_1'$, $S_0$ and $S_1$ to $S_n'$ each of which constitutes the image output S obtained for each scanning, are provided from the one-dimensional scanning image sensing device 21, as shown in FIG. 4C.

That is to say, for example, the outputs $S_n'$ to $S_{(n-1)}'$ and the outputs $S_{(n-2)}$ to $S_n$ are obtained at substantially the same level and the outputs $S_{(n-3)}'$ to $S_1'$, $S_0$ and $S_1$ to $S_{(n-3)}$ are obtained at levels lower than those of the outputs $S_n'$ to $S_{(n-2)}'$ and $S_{(n-2)}$ to $S_n$ but those outputs $S_{(n-3)}'$, $S_{(n-4)}'$, ... among the outputs $S_{(n-2)}'$ to $S_1'$ which are in the vicinity of the output $S_{(n-2)}'$ respectively assume levels which sequentially diminish from the level of the output $S_{(n-2)}'$ and those $S_{(n-3)}$ $S_{(n-4)}$ ... among the output $S_{(n-2)}$ to $S_1$ which are in the vicinity of the output $S_{(n-2)}$ respectively assume levels which sequentially diminish from the level of the output $S_{(n-2)}$.

In this case, the reason for which the outputs $S_n'$ to $S_{(n-2)}'$ and $S_{(n-2)}$ to $S_n$ assume substantially the same level is that these outputs $S_n'$ to $S_{(n-2)}'$ and $S_{(n-2)}$ to $S_n$ are the outputs of the solid-state image sensors $S_n'$ to $E_{(n-2)}'$ and $E_{(n-2)}$ to $E_n$ when they image the area of the specimen 2 on the line $LX_0$ except the points PX' and PX.

The reason for which the levels of the outputs $S_{(n-2)}'$, $S_{(n-3)}'$, $S_{(n-4)}'$, ... become gradually lower and the levels of the outputs $S_{(n-2)}$ $S_{(n-3)}$ $S_{(n-4)}$ ... become gradually lower is that the outputs $S_{(n-2)}'$, $S_{(n-3)}'$, $S_{(n-4)}'$, ... are the outputs of the solid-state image sensors $E_{(n-2)}'$, $E_{(n-3)}'$, $E_{(n-4)}'$, ... when they image the inclined area of the impression 3 which extends along the line $LX_0$ in the vicinity of the point PX', as viewed from above, and that the outputs $S_{(n-2)}$ $S_{(n-3)}$ $S_{(n-4)}$ ... are the outputs of the solid-state image sensors $E_{(n-2)}$ $E_{(n-3)}$ $E_{(n-4)}$ ... when they image the inclined area of the impression 3 which extends along the line $LX_0$ in the vicinity of the point PX, as viewed from above.

Incidentally, the specimen 2 is placed on the specimen table 1 so that line $LX_0$ is parallel to and substantially in agreement with the line of arrangement c—c of the solid-state image sensors $E_n'$ to $E_1'$, $E_0$ and $E_1$ to $E_n'$ as described previously, but, assuming that the holder 23 and the specimen table 1 lie at the aforementioned in-focus position relative to each other, the one-dimensional scanning image sensing device 21 generates, for each scanning, the abovesaid outputs $S_n'$ to $S_1'$, $S_0$ and $S_1$ to $S_n$ in the same manner a referred to above with regard to FIG. 4C. In this case, however, as shown in FIG. 4D, the outputs $S_n'$ to $S_1'$, $S_0$ and $S_1$ to $S_n$ are obtained at higher levels than in the case where the relative position of the holder 23 and the specimen table 1 is the aforesaid reference position, and the ratio of change at which the outputs $S_{(n-2)}'$, $S_{(n-3)}'$, $S_{(n-4)}'$, ... progressively diminish and the ratio of change at which the outputs $S_{(n-2)}$ $S_{(n-3)}$ $S_{(n-4)}$, ... progressively diminish are both higher than in the case where the relative position of the holder 23 and the specimen table 1 is the abovementioned reference position.

The image output S of the one-dimensional scanning image sensing device 21, which is provided therefrom in the sequential order $S_n'$ to $S_1'$, $S_0$ $S_1$ to $S_n$ for each scanning, is applied to an arithmetic processing circuit 51.

Figure 6:
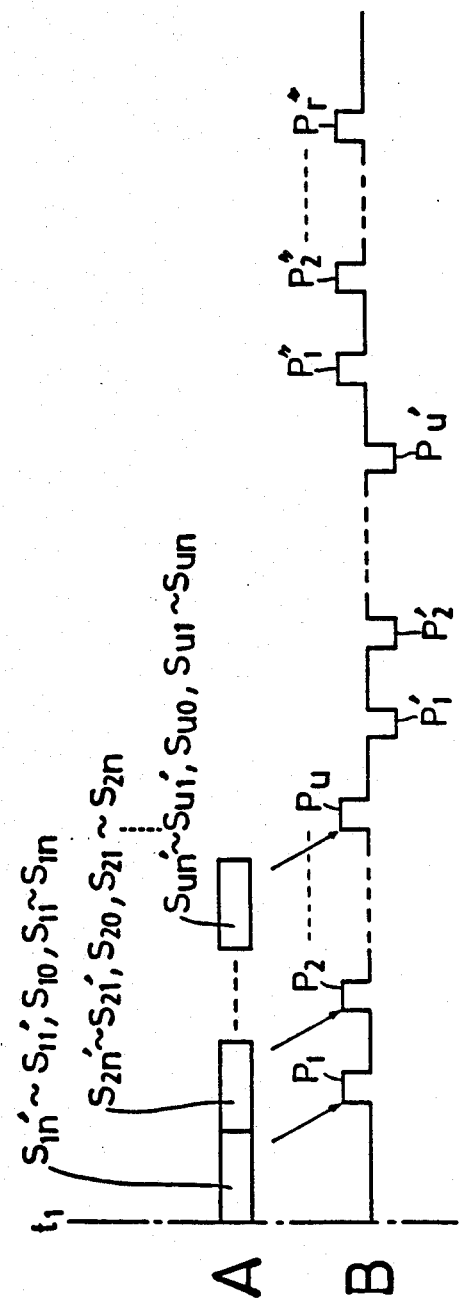
FIGS. 6, 7 and 8 are signal arrangement diagrams explanatory of the electrical system shown in FIG. 5.

Now, the outputs $S_n'$ to $S_1'$, $S_0$ and $S_1$ to $S_n$ which are sequentially obtained from the one-dimensional scanning image sensor 21 by u scanning operations starting from a certain time point $t_1$ are represented by first outputs $S_{1n}'$ to $S_{11}'$, $S_{10}$ and $S_{11}$ to $S_{1n}$; second outputs $S_{2n}'$ to $S_{21}'$, $S_{20}$ and $S_{21}$ to $S_{2n}$; ... and uth outputs $S_{un}'$ to $S_{u1}'$, $S_{u0}$ and $S_{u1}$ to $S_{un}$, respectively, as shown in FIG. 6A.

Then, the arithmetic processing circuit 51 obtains from the ith (where i=1, 2, ... u) outputs $S_{in}'$ to $S_{i1}'$, $S_{i0}$ and $S_{i1}$ to $S_{in}$ difference outputs $\Delta S_{in}'$, $\Delta S_{i(n-1)}'$, ... $\Delta S_{i1}'$, $\Delta S_{i1}$, $\Delta S_{i2}$ ... $\Delta S_{in}$ which are respectively represented by $$\Delta S_{in}' = S_{in}' - S_{i(n-1)}'$$

$$\Delta S_{i(n-1)}' = S_{i(n-1)}' - S_{i(n-2)}'$$

$$\Delta S_{i1}' = S_{i1}' - S_{i0}$$

$$\Delta S_{i1} = S_{i1} - S_{i0}$$

$$\Delta S_{i2} = S_{i2} - S_{i1}$$

.
.
.

$$\Delta S_{in} = S_{in} - S_{i(n-1)}$$

and the arithmetic processing circuit 51 decides and stores a maximum one of the difference outputs $\Delta S_{in}'$ to $\Delta S_{i1}'$ and $\Delta S_{i1}$ to $\Delta S_{in}$ (which maximum difference output will hereinafter be identified by $\Delta S_i$) and outputs a positive pulse $P_i$ as shown in FIG. 6B.

In this way, positive pulses $P_1$, $P_2$, ... $P_u$ are sequentially provided from the arithmetic processing circuit 51.

These positive pulses $P_1$, $P_2$, ... $P_u$ are supplied via a motor drive circuit 52 to the aforementioned motor 10.

When supplied with the positive pulses $P_1$, $P_2$, ... $P_u$ one after another, the motor 10 rotates in the forward direction step by step.

Consequently, the specimen table 1 moves up from the reference position step by step.

In this, case, the gear ratio between the gears 12 and 13, the gear ratio between the gears 13 and 8 and the pitches of the screw of the threaded shaft 9 and the female screw 7 of the tubular member 6 are selected so that the highest position of the specimen table 1 up to which it is raised step by step is above the aforesaid in-focus position.

After generating the positive pulses $P_1$ to $P_u'$ the arithmetic processing circuit 51 yields u negative pulses $P_1'$ to $P_u'$ one after another, as shown in FIG. 6B.

These negative pulses $P_1'$ to $P_u'$ are provided via the motor drive circuit 52 to the motor 10.

When supplied with the negative pulses $P_1'$, $P_2'$, ... $P_u'$ in the sequential order, the motor 10 rotates in the reverse direction step by step.

In consequence, the specimen table 1 moves down from the abovesaid raised position step by step correspondingly, and the specimen table 1 thus returns to the reference position.

Moreover, the arithmetic processing circuit 51 decides a maximum value of the aforesaid maximum difference outputs $\Delta S_1'$ $\Delta S_2$, ... $\Delta S_u$ (which maximum value will hereinafter be identified as an rth maximum difference output $\Delta S_r$ among the maximum difference outputs) before completion of the sequential generation of the negative pulses $P_1'$ to $P_u'$, or after generating the pulse $P_u'$.

Then, after generating the pulse $P_u'$, the arithmetic processing circuit outputs r positive pulses $P_1''$ to $P_r''$.

These positive pulses $P_1''$ to $P_u''$ are provided via the motor drive circuit 52 to the motor 10.

Accordingly, the motor 10 rotates again in the forward direction step by step and the specimen table 1 moves up step by step correspondingly and stays at the raised position.

Incidentally, the abovementioned maximum difference output $S_r$ among the maximum difference outputs $\Delta S_1'$ $\Delta S_2'$ ... $\Delta S_u$ is obtained from the output $S_{rn}'$ to $S_{r1}'$, $S_{r0}$ and $S_{r1}$ to $S_{rn}$ which are provided from the one-dimensional scanning image sensing device 21 at high levels in the case where the one-dimensional image sensing device 21 scans the specimen 2 in the in-focus state, as will be seen from the description previously given in connection with FIG. 4D.

Further, the maximum difference outputs among the maximum difference outputs $\Delta S_1'$ $\Delta S_2'$ ... $\Delta S_u$ except the maximum difference output $\Delta S_r$ are obtained from the outputs of the one-dimensional scanning image sensing device 21 which are obtained at low levels in the case where the one-dimensional scanning image sensing device 21 scans the specimen 2 in the out-of-focus state, as will be seen from the description previously given in respect of FIG. 4C.

Accordingly, the position up to which the specimen table 1 is brought up step by step on the basis of the pulses $P_1''$ to $P_r''$ as mentioned above is the aforesaid in-focus position where the one-dimensional scanning image sensing device 21 scans the specimen 2 under the in-focus condition.

Therefore, after the specimen table 1 is brought to the in-focus position, the image output S of the one-dimensional scanning image sensing device 21 is obtained at a high level.

After the specimen table 1 is brought to the in-focus position as described above, the arithmetic processing circuit 51 produces m negative pulses $G1_1$ to $G1_m$.

These m negative pulses $G1_1$ to $G1_m$ are provided via a motor drive circuit 53 to the motor 35.

By sequential application of the pulses $G1_1$, $G1_2'$ ... $G1_m'$ the motor 35 rotates in the forward direction step by step. In response to this, the aforementioned movable board 22 moves along the line b—b towards the line $LX_m'$ on the stepwise basis. In this case, the pitches of the screw 37 of the rotary shaft 36 of the motor 35 and the female screw 34 of the rod 33 of the movable board 22 are selected so that the movable board 22 moves a distance equal to the aforesaid spacing e for each step.

This provides the relationship that line $LX_m'$ on the specimen 2 is parallel to and substantially in agreement with the line of arrangement c—c of the solid-state image sensors $E_n'$ to $E_1'$, $E_0$ and $E_1$ to $E_n$.

Figure 7:
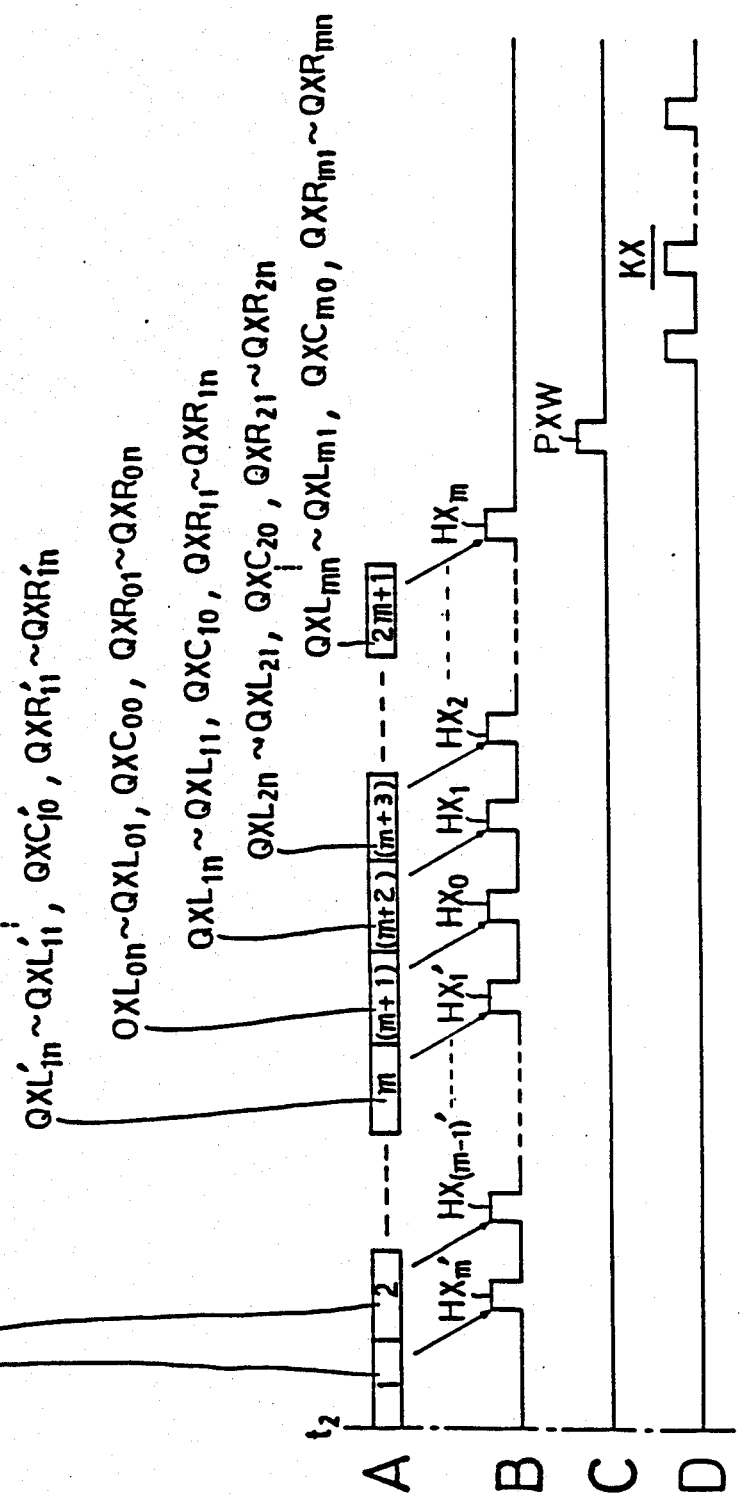

A plurality of sets of the outputs $S_n'$ to $S_1'$, $S_0$ and $S_1$ to $S_n'$ which are sequentially produced by (2m+1) scanning operations from a time point $t_2$ after the line $LX_m'$ on the specimen 2 has been brought into substantial agreement with the line of arrangement c—c as described just above, will hereinafter be identified as outputs $QXL_{mn}'$ to $QXL_{m1}'$, $QCX_{m0}'$ and $QXR_{m1}'$ to $QXR_{mn}'$ by first scanning; outputs $QXL(m-1)n'$ to $QXL_{(m-1)1}'$, $QXC_{(m-1)0}'$ and $QXR_{(m-1)1}'$ to $QXR_{(m-1)n}'$ by second scanning; ... outputs $QXL_{1n}'$ to $QXL_{11}'$, $QXC_{10}'$ and $QXR_{11}'$ to $QXR_{1n}'$ by mth scanning; outputs $QXL_{on}$ to $QXL_{01}$, $QXC_{00}$ and $QXR_{01}$ to $QXR_{0n}$ by (m+1)th scanning; outputs $QXL_{1n}$ to $QXL_{11}$, $QXC_{10}$ and $QXR_{11}$ to $QXR_{1n}$ by (m+2)th scanning; outputs $QXL_{2n}$ to $QXL_{21}$, $QXC_{20}$ and $QXR_{21}$ to $QXR_{2n}$ by (m+3)th scanning; ... and outputs $QXL_{mn}$ to $QXL_{m1}$, $QXC_{m0}$ and $QXR_{m1}$ to $QXL_{mn}$ by (2m+1)th scanning, respectively, in the same manner as described previously with respect FIG. 6A, as shown in FIG. 7A.

Then the arithmetic processing circuit 51 stores the abovesaid outputs $QXL_{jn}'$ to $QXL_{j1}'$, $QXC_{j0}'$ and $QXR_{j1}'$ to $QXR_{jn}'$ of the j'th (j'=m, (m−1), ... 1) scanning and obtains difference outputs $\Delta QXL_{jn}'$, $\Delta QXL_{j(n-1)}'$, ... $\Delta QXL_{j1}'$, $\Delta QXR_{j1}'$ $W\Delta QXR_{j2}'$, ... $\Delta QXR_{jn}'$ which are respectively represented by $$\Delta QXL_{jn}' = QXL_{jn}' - QXL_{j(n-1)}'$$

$$\Delta QXL_{j(n-1)}' = QXL_{j(n-1)}' - QXL_{j(n-2)}'$$

$$\Delta QXL_{j1}' = QXL_{j1}' - QXC_{j0}'$$

$$\Delta QXR_{j1}' = QXR_{j1}' - QXC_{j0}'$$

$$\Delta QXR_{j2}' = QXR_{j2}' - QXR_{j1}'$$

$$\Delta QXR_{jn}' = QXR_{jn}' - QXR_{j(n-1)}'$$

Then the arithmetic processing circuit 51 arrays and stores the abovesaid difference outputs $\Delta QXL_{j1}'$ to $\Delta QXL_{jn}'$ in this order.

Then the arithmetic processing circuit 51 detects the position on the array of the difference outputs where a difference output of a zero value appears for the first time after a plurality of difference outputs of positive values appear one after another (which output will hereinafter be identified as $\Delta QXL_j'$), as viewed from the side of the difference output $\Delta QXL_{j1}'$ to the side of the difference output $QXL_{jn}'$.

Thereafter the arithmetic processing circuit 51 stores an output which represents the array length from the position of the difference output $\Delta QXL_j'$ to the position of the difference output $\Delta QXL_{j1}'$ (which output will hereinfter be identified as $WXL_j'$).

Furthermore, the arithmetic processing circuit 51 similarly detects the position on the array of the difference outputs where a difference output of a zero value appears for the first time after a plurality of difference outputs of positive values appear one after another (which output will hereinafter be identified as $\Delta QXR_j'$), as viewed from the side of the difference output $\Delta QXR_{j1}'$ to the side of the difference output $\Delta QXR_{jn}'$.

Then the arithmetic processing circuit 51 stores an output which represents the array length from the position of the difference output $\Delta QXR_j'$ to the position of the difference output $\Delta QXR_{j1}'$ (which output will hereinafter be identified as $WXR_j'$).

Then the arithmetic processing circuit 51 obtains, from the outputs $WXL_j'$ and $QXR_j'$ representing the abovesaid array lengths, an output $MX_j'$ represented by $$MX_j' = WXL_j' + WXR_j'$$

and stores it. Then the arithmetic processing circuit 51 outputs a pulse $HX_j'$, as shown in FIG. 7B.

Furthermore the arithmetic processing circuit 51 stores the abovesaid outputs $QXL_{0n}$ to $QXL_{01}$, $QXC_{00}$ and $QXR_{01}$ to $QXR_{0n}$ of the (m+1)th scanning and obtains difference outputs $\Delta QXL_{0n}$, $\Delta QXL_{0(n-1)}$, ... $\Delta QXL_{01}$, $\Delta QXR_{01}$, $\Delta QXR_{02}$, ... $\Delta QXR_{0n}$ which are respectively represented by $$\Delta QXL_{0n} = QXL_{0n} - QXL_{0(n-1)}$$

$$\Delta QXL_{0(n-1)} = QXL_{0(n-1)} - QXL_{0(n-2)}$$

$$\Delta QXL_{01} = QXL_{01} - QXC_{00}$$

$$\Delta QXR_{01} = QXR_{01} - QXC_{00}$$

$$\Delta QXR_{02} = QXR_{02} - QXR_{01}$$

$$\Delta QXR_{0n} = QXR_{0n} - QXR_{0(n-1)}$$

Then the arithmetic processing circuit 51 arrays and stores the abovesaid difference outputs $\Delta QXL_{01}$ to $\Delta QXL_{0n}$ in this order.

Then the arithmetic processing circuit detects the position on the array of the difference outputs where a difference output of a zero value appears for the first time after a plurality of difference outputs of positive values appear one after another (which output will hereinafter be identified as $\Delta QXL_0$), as viewed from the side of the difference output $\Delta QXL_{01}$ to the side of the difference output $QXL_{0n}$.

Thereafter the arithmetic processing circuit 51 stores an output which represents the array length from the position of the difference output $\Delta QXL_0$ to the position of the difference output $\Delta QXL_{01}$ (which output will hereinfter be identified as $WXL_0$).

Furthermore, the arithmetic processing circuit 51 similarly detects the position on the array of the difference outputs where a difference output of a zero value appears for the first time after a plurality of difference outputs of positive values appear one after another (which output will hereinafter be identified as $\Delta QXR_0$), as viewed from the side of the difference output $\Delta QXR_{01}$ to the side of the difference output $\Delta QXR_{0n}$.

Then the arithmetic processing circuit 51 stores an output which represents the array length from the position of the difference output $\Delta QXR_0$ to the position of the difference output $\Delta QXR_{01}$ (which output will hereinafter be identified as $WXR_0$).

Then the arithmetic processing circuit obtains, from the outputs $WXL_0$ and $QXR_0$ representing the abovesaid array lengths, an output $MX_0$ represented by $$MX_0 = WXL_0 + WXR_0$$

and stores it. Then the arithmetic processing circuit 51 outputs a pulse $HX_0$, as shown in FIG. 7B.

Furthermore the arithmetic processing circuit 51 stores the aboveasaid outputs $QXL_{jn}$ to $QXL_{j1}$, $QXC_{j0}$ and $QXR_{j1}$ to $QXR_{jn}$ of the jth (j=1, 2 ... m) scanning and obtains difference outputs $\Delta QXL_{jn}$, $\Delta QXL_{j(n-1)}$, ... $\Delta QXL_{j1}$, $\Delta QXR_{j1}$, $\Delta QXR_{j2}$, ... $\Delta QXR_{jn}$ which are respectively represented by $$\Delta QXL_{jn} = QXL_{jn} - QXL_{j(n-1)}$$

$$\Delta QXL_{j(n-1)} = QXL_{j(n-1)} - QXL_{j(n-2)}$$

.
.
.

$$\Delta QXL_{j1} = QXL_{j1} - QXC_{j0}$$

$$\Delta QXR_{j1} = QXR_{j1} - QXC_{j0}$$

$$\Delta QXR_{j2} = QXR_{j2} - QXR_{j1}$$

.
.
.

$$\Delta QXR_{jn} = QXR_{jn} - QXR_{j(n-1)}$$

Then the arithmetic processing circuit 51 arrays and stores the aboveasaid difference outputs $\Delta QXL_{j1}$ to $\Delta QXL_{jn}$ in this order.

Then the arithmetic processing circuit detects the position on the array of the difference outputs where a difference output of a zero value appears for the first time after a plurality of difference outputs of positive values appear one after another (which output will hereinafter be identified as $\Delta QXL_j$), as viewed from the side of the difference output $\Delta QXL_{j1}$ to the side of the difference output $QXL_{jn}$.

Thereafter the arithmetic processing circuit 51 stores an output which represents the array length from the position of the difference output $\Delta QXL_j$ to the position of the difference output $\Delta QXL_{j1}$ (which output will hereinfter be identified as $WXL_j$).

Furthermore, the arithmetic processing circuit 51 similarly detects the position on the array of the difference outputs where a difference output of a zero value appears for the first time after a plurality of difference outputs of positive values appear one after another (which output will hereinafter be identified as $\Delta QXR_j$), as viewed from the side of the difference output $\Delta QXR_{j1}$ to the side of the difference output $\Delta QXR_{jn}$.

Then the arithmetic processing circuit 51 stores an output which represents the array length from the position of the difference output $\Delta QXR_j$ to the position of the difference output $\Delta QXR_{j1}$ (which output will hereinafter be identified as $WXR_j$).

Then the arithmetic processing circuit 51 obtains, from the outputs $WXL_j$ and $QXR_j$ representing the aboveasaid array lengths, an output $MX_j$ represented by $$MX_j = WXL_j + WXR_j$$

and stores it. Then the arithmetic processing circuit 51 outputs a positive pulse $HX_j$, as shown in FIG. 7B.

In the manner described above, the arithmetic processing circuit 51 provides positive pulses $HX_m'$, $HX_{(m-1)}'$, ... $HX_1'$, $HX_0$, $HX_1$, $HX_2$, ... $HX_m$ one after another.

These pulses $HX_m'$, $HX_{(m-1)}'$, ... $HX_1'$, $HX_0'$, $HX_1$, $HX_2$, ... $HX_m$ are applied via the motor drive circuit 53 to motor 35.

Supplied with the pulses $HX_m'$, $HX_{(m-1)}'$, ... $HX_1'$, $HX_0$, $HX_1$, $HX_2$, ... $HX_m$ one after another, the motor 35 rotates in the forward direction step by step. Consequently, the movable board 22 moves along the aforementioned line b—b step by step, the distance of movement for each step being equal to the aforesaid interval.

By such step-by-step movement of the movable board 22, the aforesaid line c—c held so far at the position relative to the holder 23 where the line is substantially in agreement with the line $LX_m'0$ is brought into substantial agreement with the lines $LX_{(m-1)}'$, $LX_{(m-2)}'$, ... $LX_1'$, $LX_0'$, $LX_1$, ... $LX_m$ one after another.

Accordingly, the output $MXL_j'$ of the output $MX_j$ represents the length from the central position O of the impression 3 of the specimen 2 to the marginal edge thereof on the side of the point PX' on the aforementioned line $LX_j'$.

The reason is as follows: The output $WXL_j'$ is representative of the array length from the position of the aforesaid difference output $\Delta QXL_j'$ to the position of the difference output $\Delta QXL_{j1}'$. On the other hand, the difference output $\Delta QXL_j'$ is the difference output of a zero value that appears for the first time on the array after a plurality of difference outputs of positive values appear one after another, as viewed from the side of the difference output $\Delta QXL_{j1}'$ to the side of the difference output $\Delta QXL_{jn}'$. Accordingly, the position of the difference output $\Delta QXL_j'$ on the array corresponds to the marginal edge of the impression 3 on the line $LX_j'$ on the side of the point PX', as will be evident from the description given previously of the general outputs $S_n'$, $S_{(n-1)}'$, ... $S_1'$, $S_0$, $S_1$, $S_2$, ... $S_{(n-1)}$, $S_n$ with reference to FIGS. 4C and D.

For the same reason as mentioned above, the output $WXR_j'$ of the output $MX_j'$ represents the length of the impression 3 of the specimen 2 on the line $LX_j'$ from the central position O of the impression 3 to its marginal edge on the side of the point PX on the line $LX_j'$.

Accordingly, the output $MX_j'$ represents the length of the impression 3 on the line $LX_j'$.

Furthermore, for the same reason as given above, the outputs $MX_0$ and $MX_j$ represents the lengths of the impression 3 on the lines $LX_0$ and $LX_j$, respectively.

Moreover, after generating the pulses $HX_m'$, $HX_{(m-1)}'$ ... $HX_1'$, $HX_0$, $HX_1$, $HX_2$, ... $HX_m$, the arithmetic processing circuit 51 yields one switching pulse PXW, as shown in FIG. 7C.

This switching pulse PXW is provided to a motor drive circuit 54.

On the other hand, the motor drive circuit 54 has connected thereto the switches 39 and 39' for engagement with the engaging pin 38 of the holder 23.

Since the holder 23 stays at the first rotational position, the switch 39 is operative when the switching pulse PXW is obtained.

When supplied with the switching pulse PXW during the operation of the switch 39, the motor drive circuit 54 generates sequential pulses KX, as shown in FIG. 7D.

Supplied with the sequential pulses KX, the motor 30 rotates in the forward direction step by step. In consequence, the holder 23 turns in the forward direction.

Then, when the holder 23 turns until the engaging pin is brought into engagement with the switch 39', the switch 39' is activated.

As a result of this, the pulses KX are no more generated from the motor drive circuit 54 and the motor 30 stops, and consequently the holder 23 also stops.

When the holder 23 is thus stopped, it assumes such a rotational position relative to the specimen 2 that the line of arrangement c—c of the solid-state image sensors $E_n'$ to $E_1'$, $E_0$ and $E_1$ to $E_n$ of the one-dimensional scanning image sensing device 21 substantially agrees with the aforementioned line $LY'_0$ on the specimen 2 (which rotational position will hereinafter be referred to as the second rotational position).

Figure 8:
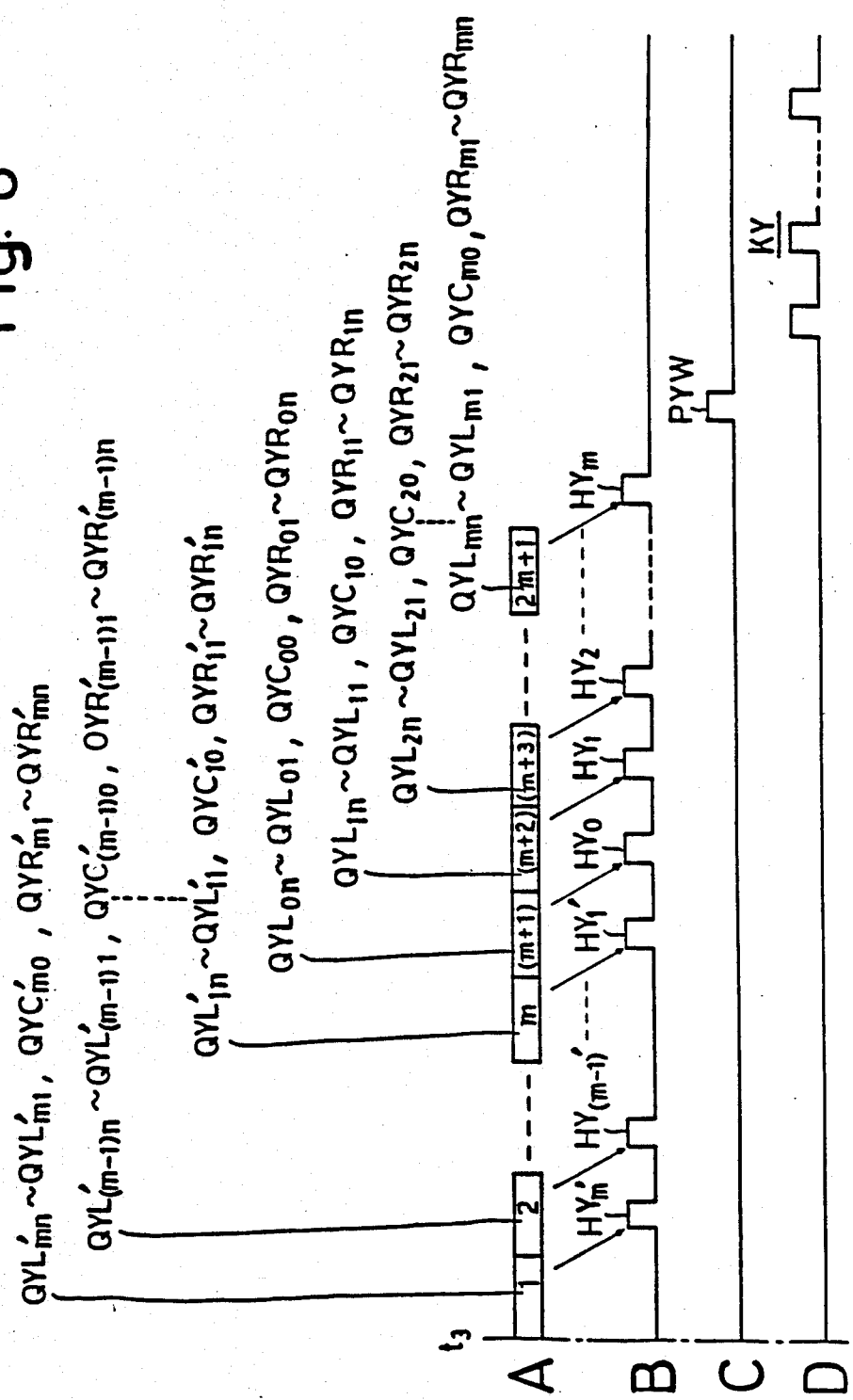

A plurality of sets of the outputs $S_n'$ to $S_1'$, $S_0$ and $S_1$ to $S_n'$ which are sequentially produced by $(2m+1)$ scanning operations from a time point $t_3$ after the holder 23 has been brought to the second rotational position where the line of arrangement c—c substantially agrees with the line $LY_m'$ on the specimen 2 as described just above, will hereinafter be identified as outputs $QYL_{mn}'$ to $QYL_{m1}'$, $QYC_{m0}'$ and $QYR_{m1}'$ to $QYR_{mn}'$ by first scanning; outputs $QYL_{(m-1)n}'$ to $QYL_{(m-1)1}'$, $QYC_{(m-1)0}'$ and $QYR_{(m-1)1}'$ to $QYR_{(m-1)n}'$ by second scanning; ... outputs $QYL_{1n}'$ to $QYL_{11}'$, $QYC_{10}'$ and $QYR_{11}'$ to $QYR_{1n}'$ by mth scanning; outputs $QYL_{0n}$ to $QYL_{01}$, $QYC_{00}$ and $QYR_{01}$ to $QYR_{0n}$ by $(m+1)$th scanning; outputs $QYL_{1n}$ to $QYL_{11}'$ $QYC_{10}$ and $QYR_{11}$ to $QYR_{1n}$ by $(m+2)$th scanning; outputs $QYL_{2n}$ to $QYL_{21}'$ $QYC_{20}$ and $QYR_{21}$ to $QYR_{2n}$ by $(m+3)$th scanning; ... and outputs $QYL_{mn}$ to $QYL_{m1}'$ $QYC_{m0}$ and $QYR_{m1}$ to $QYL_{mn}$ by $(2m+1)$th scanning, respectively, in the same manner as described previously with respect FIG. 7A, as shown in FIG. 8A.

Then the arithmetic processing circuit 51 stores the abovesaid outputs $QYL_{jn}'$ to $QYL_{j1}'$, $QYC_{j0}'$ and $QYR_{j1}'$ to $QYR_{jn}'$ of the j'th (j'=m, (m−1), ... 1) scanning and obtains difference outputs $\Delta QYL_{jn}'$, $\Delta QYL_{j(n-1)}'$, ... $\Delta QYL_{j1}'$, $\Delta QYR_{j1}'$, $\Delta QYR_{j2}'$, ... $\Delta QYR_{jn}'$ which are respectively represented by $$\Delta QYL_{jn}' = QYL_{jn}' - QYL_{j(n-1)}'$$

$$\Delta QYL_{j(n-1)}' = QYL_{j(n-1)}' - QYL_{j(n-2)}'$$

$$\Delta QYL_{j1}' = QYL_{j1}' - QYC_{j0}'$$

$$\Delta QYR_{j1}' = QYR_{j1}' - QYC_{j0}'$$

$$\Delta QYR_{j2}' = QYR_{j2}' - QYR_{j1}'$$

$$\Delta QYR_{jn}' = QYR_{jn}' - QYR_{j(n-1)}'$$

Then the arithmetic processing circuit 51 arrays and stores the abovesaid difference outputs $\Delta QYL_{j1}'$ to $\Delta QYL_{jn}'$ in this order.

Then the arithmetic processing circuit 51 detects the position on the array of the difference outputs where a difference output of a zero value appears for the first time after a plurality of difference outputs of positive values appear one after another (which output will hereinafter be identified as $\Delta QYL_j'$), as viewed from the side of the difference output $\Delta QYL_{j1}'$ to the side of the difference output $QYL_{jn}'$.

Thereafter the arithmetic processing circuit 51 stores an output which represents the array length from the position of the difference output $\Delta QYL_j'$ to the position of the difference output $\Delta QYL_{j1}'$ (which output will hereinafter be identified as $WYL_j'$).

Furthermore. the arithmetic processing circuit 51 similarly detects the position on the array of the difference outputs where a difference output of a zero value appears for the first time after a plurality of difference outputs of positive values appear one after another (which output will hereinafter be identified as $\Delta QYR_j'$), as viewed from the side of the difference output $\Delta QYR_{j1}'$ to the side of the difference output $\Delta QYR_{jn}'$.

Then the arithmetic processing circuit 51 stores an output which represents the array length from the position of the difference output $\Delta QYR_j'$ to the position of the difference output $\Delta QYR_{j1}'$ (which output will hereinafter be identified as $WYR_j'$).

Then the arithmetic processing circuit 51 obtains, from the outputs $WYL_j'$ and $QYR_j'$ representing the abovesaid array lengths, an output $MY_j'$ represented by $$MY_j' = WYL_j' + WYR_j'$$

and stores it. Then the arithmetic processing circuit outputs a pulse $HY_j'$, as shown in FIG. 8B.

Furthermore the arithmetic processing circuit 51 stores the abovesaid outputs $QYL_{0n}$ to $QYL_{01}$, $QYC_{00}$ and $QYR_{01}$ to $QYR_{0n}$ of the $(m+1)$th scanning and obtains difference outputs $\Delta QYL_{0n}$, $\Delta QYL_{0(n-1)}$, ... $\Delta QYL_{01}$, $\Delta QYR_{01}$, $\Delta QYR_{02}$, ... $\Delta QYR_{0n}$ which are respectively represented by $$\Delta QYL_{0n} = QYL_{0n} - QYL_{0(n-1)}$$

$$\Delta QYL_{0(n-1)} = QYL_{0(n-1)} - QYL_{0(n-2)}$$

$$\Delta QYL_{01} = QYL_{01} - QYC_{00}$$

$$\Delta QYR_{01} = QYR_{01} - QYC_{00}$$

$$\Delta QYR_{02} = QYR_{02} - QYR_{01}$$

$$\Delta QYR_{0n} = QYR_{0n} - QYR_{0(n-1)}$$

Then the arithmetic processing circuit 51 arrays and storeds the abovesaid difference outputs $\Delta QYL_{01}$ to $\Delta QYL_{0n}$ in this order.

Then the arithmetic processing circuit 51 detects the position on the array of the difference outputs where a difference output of a zero value appears for the first time after a plurality of difference outputs of positive values appear one after another (which output will hereinafter be identified as $\Delta QYL_0$), as viewed from the side of the difference output $QYL_{01}$ to the side of the difference output $\Delta QYL_{0n}$.

Thereafer the arithmetic processing circuit 51 stores an output which represents the array length from the position of the difference output $\Delta QYL_0$ to the position of the difference output $\Delta QYL_{01}$ (which output will hereinafter be identified as $WYL_0$).

Furthermore, the arithmetic processing circuit 51 similarly detects the position on the array of the difference outputs where a difference output of a zero value appears for the first time after a plurality of difference outputs of positive values appear one after another (which output will be indentified as $\Delta QYR_0$), as viewed from the side of the difference output $\Delta QYR_{01}$ to the side of the difference output $\Delta QYR_{0n}$.

Then the arithmetic processing circuit 51 stores an output which represents the array length from the position of the difference output $\Delta QYR_0$ to the position of the difference output $\Delta QYR_{01}$ (which output will hereinafter be identified as $WYR_0$).

Then the arithmetic processing circuit 51 obtains, from the output $WYL_0$ and $QYR_0$ representing the abovesaid aray lengths, an output $MY_0$ represented by $$MY_0 + WYL_0 = WYR_0$$

and stores it. Then the arithmetic processing circuit outputs a pulse $HY_0$, as shown in FIG. 8B.

Futhermore, the arithmetic processing circuit 51 stores the abovesaid outputs $QYL_{jn}$ to $QYL_{j1}$, $QYC_{j0}$ and $QYR_{j1}$ to $QYR_{jn}$ of the jth (j=1, 2 ... m) scanning and obtains difference outputs $\Delta QYL_{jn}$, $\Delta QYL_{j(n-1)}$, ... $\Delta QYL_{j1}$, $\Delta QYR_{j1}$, $\Delta QYR_{j2}$, ... $\Delta QYR_{jn}$ which are respectively represented by $$\Delta QYL_{jn} = QYL_{jn} - QYL_{j(n-1)}$$

$$\Delta QYL_{j(n-1)} = QYL_{j(n-1)} - QYL_{j(n-2)}$$

.

$$\Delta QYL_{j1} = QYL_{j1} - QYC_{j0}$$

$$\Delta QYR_{j1} = QYR_{j1} - QYC_{j0}$$

$$\Delta QYR_{j2} = QYR_{j2} - QYR_{j1}$$

.

$$\Delta QYR_{jn} = QYR_{jn} - QYR_{j(n-1)}$$

Then the arithmetic processing circuit 51 arrays and stores the abovesaid difference outputs $\Delta QYL_{j1}$ to $\Delta QYL_{jn}$ in this order.

Then the arithmetic processing circuit detects the position on the array of the difference outputs where a difference output of a zero value appears for the first time after a plurality of difference outputs of positive values appear one after another (which output will hereinafter be identified as $\Delta QYL_j$), as viewed from the side of the difference output $\Delta QYL_{j1}$ to the side of the difference output $QYL_{jn}$.

Thereafter the arithmetic processing circuit 51 stores an output which represents the array length from the position of the difference output $\Delta QYL_j$ to the position of the difference output $\Delta QYL_{j1}$ (which output will hereinfter be identified as $WYL_j$).

Furthermore, the arithmetic processing circuit 51 similarly detects the position on the array of the difference outputs where a difference output of a zero value appears for the first time after a plurality of difference outputs of positive values appear one after another (which output will hereinafter be identified as $\Delta QYR_j$), as viewed from the side of the difference output $\Delta QYR_{j1}$ to the side of the difference output $\Delta QYR_{jn}$.

Then the arithmetic processing circuit 51 stores an output which represents the array length from the position of the difference output $\Delta QYR_j$ to the position of the difference output $\Delta QYR_{j1}$ (which output will hereinafter be identified as $WYR_j$).

Then the arithmetic processing circuit 51 obtains, from the outputs $WYL_j$ and $QYR_j$ representing the abovesaid array lengths, an output $MY_j$ represented by $$MY_j = WYL_j + WYR_j$$

and stores it. Then the arithmetic processing circuit outputs a positive pulse $HY_j$, as shown in FIG. 8B.

In the manner described above, the arithmetic processing circuit 51 provides positive pulses $HY_m'$, $HY_{(m-1)}'$, ... $HY_1'$, $HY_0$, $HY_1$, $HY_2$, ... $HY_m$ one after another.

These pulses $HY_m'$, $HY_{(m-1)}'$, ... $HY_1'$, $HY_0'$, $HY_1$, $HY_2$, ... $HY_m$ are applied via the motor drive circuit 53 to motor 35.

Supplied with the pulses $HY_m'$, $HY_{(m-1)}'$, ... $HY_1'$, $HY_0$, $HY_1$, $HY_2$, ... $HY_m$ one after another, the motor 35 rotates in the forward direction step by step. Consequently, the movable board 22 moves along the aforementioned line b—b step by step, the distance of movement for each step being equal to the aforesaid interval.

By such step-by-step movement of the movable board 22, the aforesaid line c—c held so far at the position relative to the holder 23 where the line is substantially in agreement with the line $LY_m'$ is brought into substantial agreement with the lines $LY_{(m-1)}'$, $LY_{(m-2)}'$, ... $LY_1'$, $LY_0'$, $LY_1$, ... $LY_m$ one after another.

Accordingly, the output $MYL_j'$ of the output $MY_j'$ represents the length from the central position O of the impression 3 of the specimen 2 to the marginal edge thereof on the side of the point $PY'$ on the aforementioned line $LY_j'$.

The reason is as follows: The output $WYL_j'$ is representative of the array length from the position of the aforesaid difference output $\Delta QXL_j'$ to the position of the difference output $\Delta QXL_{j1}'$. On the other hand, the difference output $\Delta QXL_j'$ is the difference output of a zero value that appears for the first time on the array of the difference outputs $\Delta QXL_{j1}'$ to $\Delta QXL_{jn}'$ after a plurality of difference outputs of positive values appear one after another, as viewed from the side of the difference output $\Delta QXL_{j1}'$ to the side of the difference output $\Delta QXL_{jn}'$. Accordingly, the position of the difference output $\Delta QXL_j'$ on the array corresponds to the marginal edge of the impression 3 on the line $LY_j'$ on the side of the point $PY'$, as will be evident from the description given previously of the general outputs $S_n'$, $S_{(n-1)}'$, ... $S_1'$, $S_0$, $S_1$, $S_2$, ... $S_{(n-1)}$, $S_n$ with reference to FIGS. 4C and D.

For the same reason as mentioned above, the output WYR$_j$' of the output MY$_j$' represents the length of the impression 3 of the specimen 2 on the line LY$_j$' from the central position O of the impression 3 to its marginal edge on the side of the point PY on the line LY$_j$'.

Accordingly, the output MY$_j$' represents the length of the impression 3 on the line LY$_j$'.

Furthermore, for the same reason as given above, the outputs MY$_0$ and MY$_j$ represents the lengths of the impression 3 on the lines LY$_0$ and LY$_j$, respectively.

Moreover, after generating the pulses HY$_m$', HY$_{(m-1)}$'... HY$_1$', HY$_0$, HY$_1$, HY$_2$, ... HY$_m$, the arithmetic processing circuit 51 yields one switching pulse PYW, as shown in FIG. 8C.

This switching pulse PYW is provided to a motor drive circuit 54.

On the other hand, the motor drive circuit 54 has connected thereto the switches 39 and 39' for engagement with the engaging pin 38 of the holder 23.

Since the holder 23 stays at the second rotational position, the switch 39 is operative when the switching pulse PYW is obtained.

When supplied with the switching pulse PYW during the operation of the switch 39', the motor drive circuit 54 generates sequential pulses KY, as shown in FIG. 8D.

The sequential pulses KY are provided to the motor 30.

Supplied with the sequential pulses KY, the motor 30 rotates in the reverse direction step by step. In consequence, the holder 23 turns in the reverse direction.

Then, when the holder 23 turns until the engaging pin is brought into engagement with the switch 39, the switch 39 is activated.

As a result of this, the pulses KY are no more generated from the motor drive circuit 54 and the motor 30 stops, and consequently the holder 23 also stops.

When the holder 23 is thus stopped, it assumes the first rotational position relative to the specimen 2 that the line of arrangement c—c of the solid-state image sensors E$_n$' to E$_1$', E$_0$ and E$_1$ to E$_n$ of the one-dimensional scanning image sensing device 21 substantially agrees with the aforementioned line LX$_m$' on the specimen 2.

As described previously, the arithmetic processing circuit 51 stores the outputs MY$_m$' to MY$_1$', My$_0$ and MY$_1$ to MY$_m$ as well as the aforementioned outputs MX$_m$' to MX$_{(m-n)}$', MX$_0$ and MX$_1$ to MX$_m$.

The arithmetic processing circuit 51 detects a maximum one (which will hereinafter be identified as MX) among the outputs MX$_m$' to MX$_1$', MX$_0$ and MX$_1$ to MX$_m$ and yields the output MX. The output MX is the output MX$_0$ when the outputs MX$_m$' to MX$_1$', MX$_0$ and MX$_1$ to MX$_m$ are obtained as described above.

Likewise, the arithmetic processing circuit 51 detects a maximum one (which will hereinafter be identified as MY) of the outputs MY$_m$' to MY$_1$', MY$_0$ and MY$_1$ to MY$_m$ and yields the output MY. The output MY is the output MY$_0$ when the outputs MY$_m$' to MY$_1$', MY$_0$ and MY$_1$ to MY$_m$ are obtained as described above.

The output MX represents the length NX of the first diagonal joining the points PX and PX' of the impression 3 of the specimen 2, as will be seen from the foregoing description.

Similarly, the output MY represents the length NY of the first diagonal joining the points PY and PY' of the impression 3 of the specimen 2, as will be evident from the foregoing description.

As described above, according to the first embodiment of the indentation hardness meter of the present invention, the lengths NX and NY of the first and second diagonals of the impression 3 made in the specimen 2 can be measured.

Accordingly, the hardness of the specimen 2 can be measured from the lengths NX and NY.

In this case, according to the indentation hardness meter of the present invention described in the foregoing, the impression 3 made in the specimen 2 is imaged by one-dimensional scanning through the use of the one-dimensional image sensing device 21 and the outputs representing the lengths of the first and second diagonals of the impression 3 are obtained from the image output.

Accordingly, the indentation hardness meter of the present invention has such a great feature that the image sensing device for obtaining the first and second diagonal-length signals may be a simple, small and inexpensive one-dimensional scanning image sensing device.

Moreover, according to the indentation hardness meter of the present invention, the first and second diagonal-length signals can be obtained at high speed without scanning the entire area of the impression by the one-dimensional scanning image sensing device.

In addition, the indentation hardness meter of the present invention has such a great advantage that the entire arrangement is simple.

Next, a description will be given of a second embodiment of the indentation hardness meter of the present invention.

Figure 9:
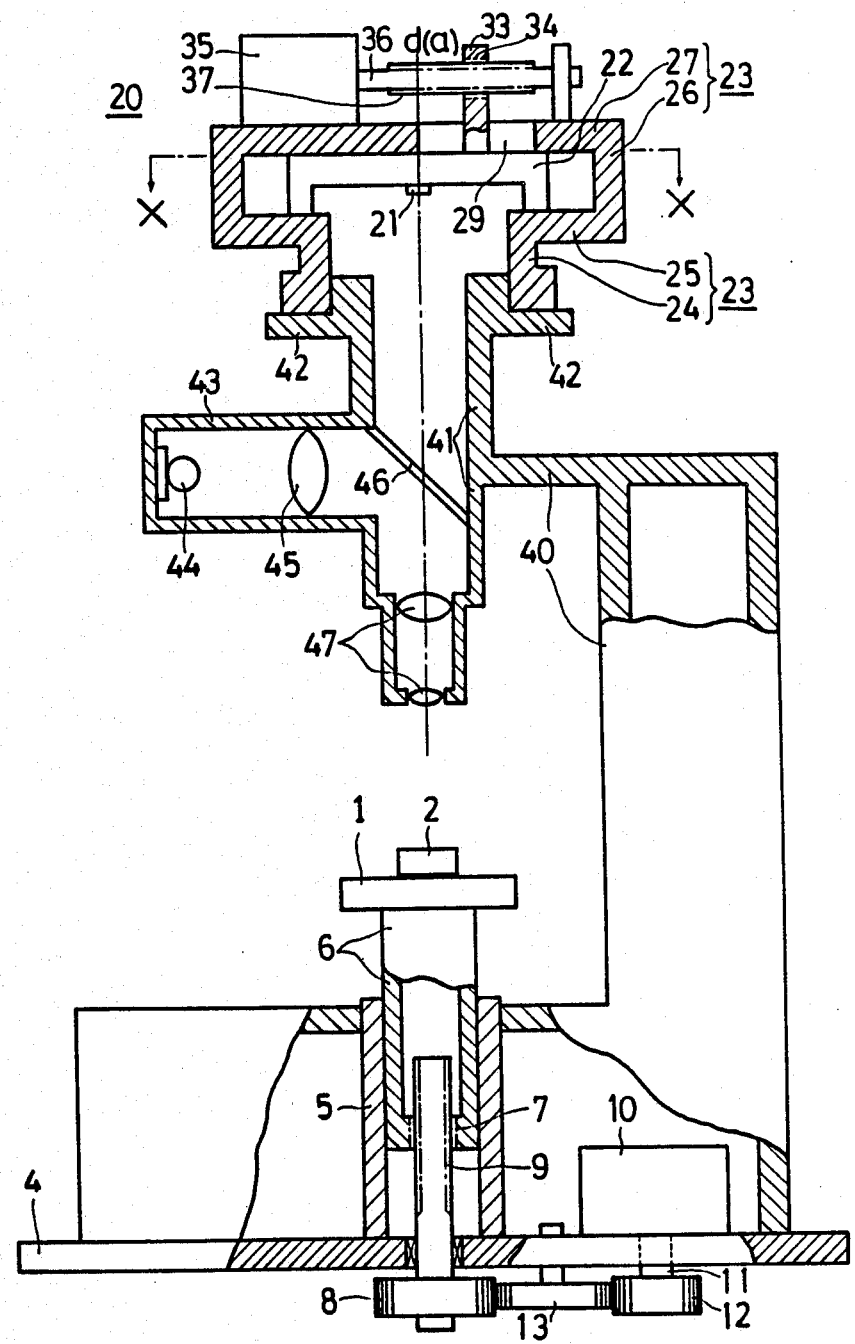
FIG. 9 is a schematic sectional view illustrating an example of the mechanical system of a second embodiment of the indentation hardness meter of the present invention.
Figure 10:
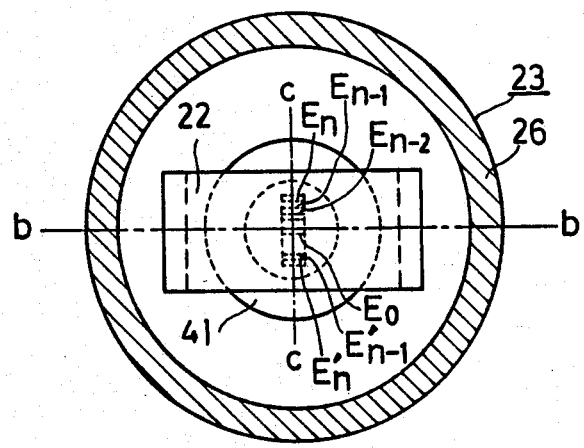
FIG. 10 is a sectional view taken on the line II—II in FIG. 9.

FIGS. 9 and 10 illustrate an example of the mechanical system of the second embodiment of the indentation hardness meter of the present invention.

In FIGS. 9 and 10, the parts corresponding to those in FIGS. 1 and 2 are identified by the same reference numerals and no detailed description will be repeated.

The mechanical system of the indentation hardness meter of the present invention shown in FIGS. 9 and 10 is identical in construction with the mechanical system of the first embodiment of the indentation hardness meter of the present invention illustrated in FIGS. 1 and 2, except in the following points:

That is to say, the motor 30 mounted on the support 40, the gear 32 provided on the rotary shaft 31 and the gear 28 provided on the tubular member 24 of the holder 23 are omitted. Further, the engaging pin 38 planted on the annular portion 25 of the holder 23 and the switches 39 and 39' for engagement with the engaging pin 38 are omitted.

Moreover, the holder 23 of the image sensing device mount 20 is fixedly disposed around the tubular member 41 by suitable fixing means (not shown), instead of being rotatably disposed around the tubular member 41.

The above is an example of the mechanical system of the second embodiment of the indentation hardness meter of the present invention.

Figure 12:
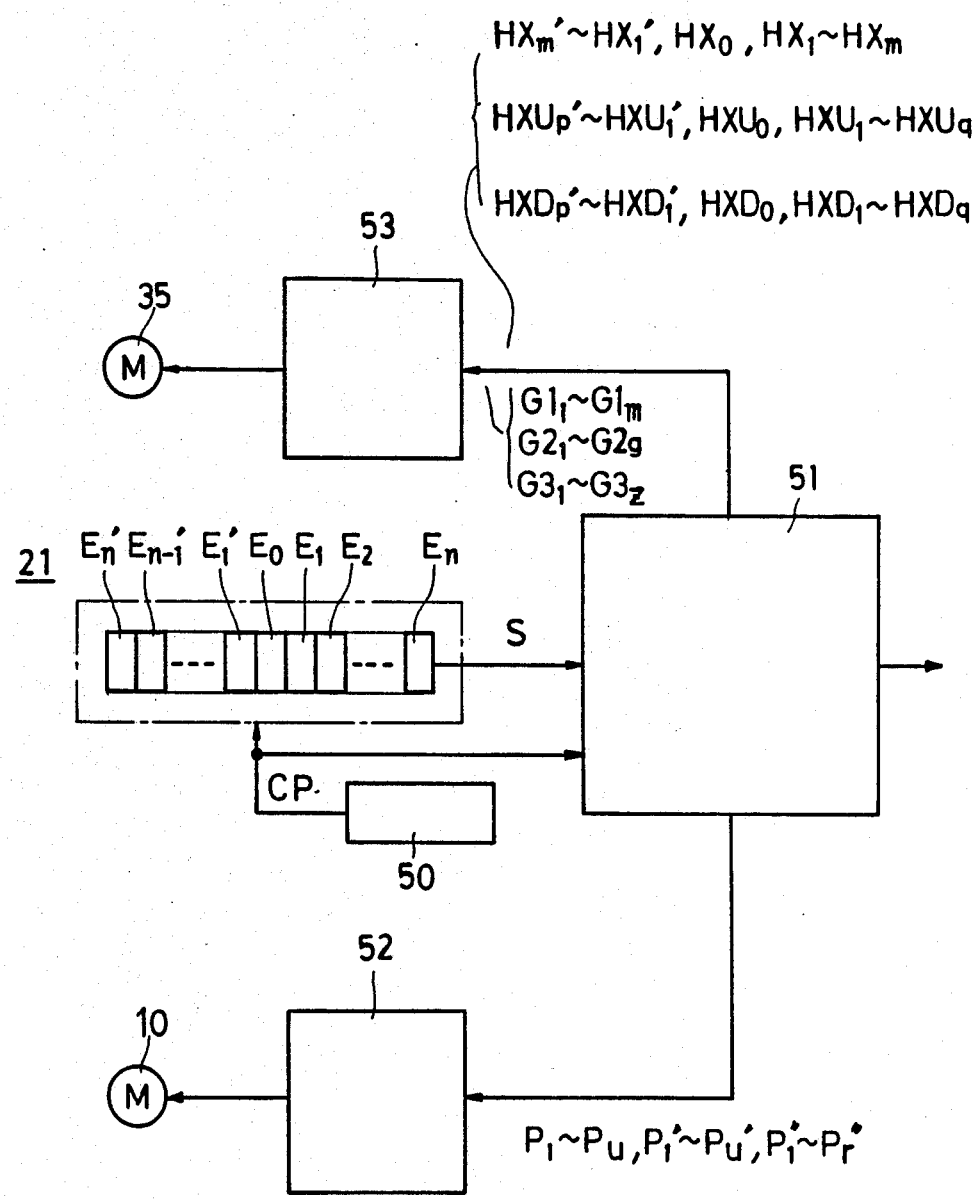
FIG. 12 is a systematic connection diagram illustrating the electrical system of the second embodiment of the indentation hardness meter of the present invention in the case of employing the mechanical system shown in FIGS. 9 and 10.

Turning next to FIG. 12, an example of the electrical system of the indentation hardness meter of the present invention which employs the mechanical system described above with regard to FIGS. 9 and 10 will be described, together with its operation.

In FIG. 12, the parts corresponding to those in FIG. 5 are identified by the same reference numerals and no detailed description will be repeated.

The electrical system illustrated in FIG. 12 is identical in construction with the system shown in FIG. 5 except the omission of the motor 30 and the motor drive circuit 54 which has connected thereto the switches 39 and 39' in the electrical system of FIG. 5.

By applying the light from the light source 44 via the lens 45, the half-mirror 46 and the lens 47 to the specimen 2 and by applying the reflected light therefrom to the one-dimensional scanning image sensing device 21 via the lens 47 and the half-mirror 46, the image output S obtained by one-dimensional scanning of the specimen is provided from the one-dimensional scanning image sensing device 21 in the same manner as described previously with respect to FIG. 5.

In this case, as shown in FIG. 12, the onedimensional scanning image sensing device 21 is driven under the control of the clock pulses CP from the clock pulse generator 50, such as depicted in FIG. 4B.

Incidentally, the one-dimensional scanning image sensing device 21 has such as arrangement that the many solid-state image sensors $E_n'$, $E_{(n-1)}'$, ... $E_1'$, $E_{0'}$ $E_{1'}$ $E_{2'}$ ... $E_n$ are electrically connected in series one after another and one-dimensionally aligned in a line on the aforesaid line c—c, as shown in FIG. 10 and in the same manner as referred to previously.

Accordingly, the image output S is obtained as photoelectric conversion outputs $S_n'$, $S_{(n-1)}'$, ... $S_1'$, $S_{0'}$ $S_{1'}$ $S_{2'}$ ... $S_n$ which are sequentially provided, by the respective scanning of the one-dimensional scanning image sensing device 21, from the solid-state image sensors $E_n'$, $E_{(n-1)}'$, ... $E_1'$, $E_{0'}$ $E_{1'}$ $E_{2'}$ ... $E_{n'}$ respectively, in the same manner as described previously in connection with FIGS. 4C and D.

Figure 11:
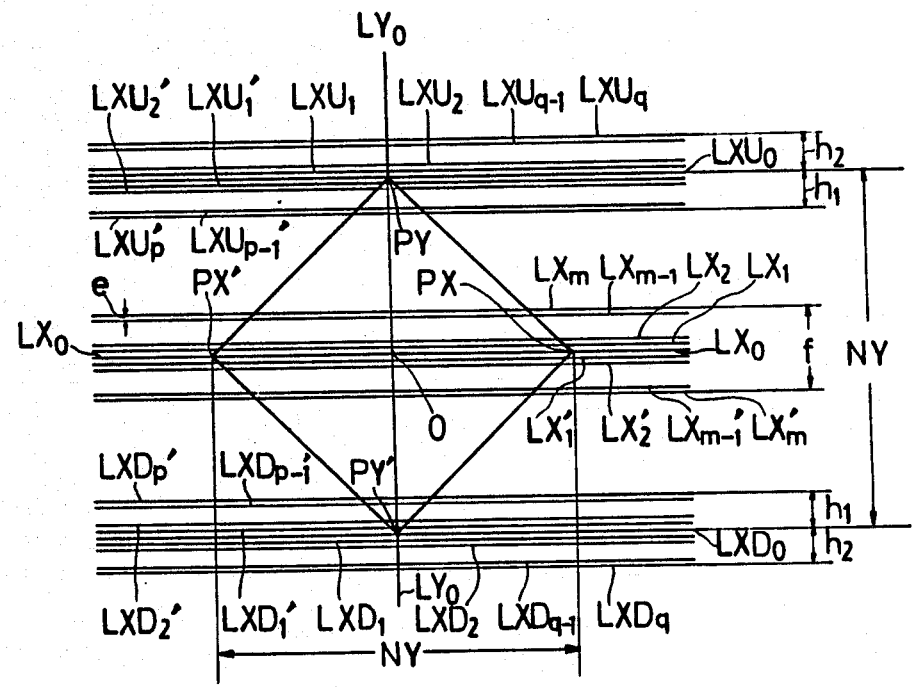
FIG. 11 is a diagram explanatory of imaging a specimen by one-dimensional scanning through the one-dimensional image sensing device.

Now, let a line, which extends in the plane containing the surface of the specimen 2 and contains the first diagonal joining a pair of opposing points PX and PX' of the quadrangular pyramidal impression 3 made in the specimen 2 on the specimen table 1 as shown in FIG. 3, be represented by $LX_0$ as shown in FIG. 11 and in the same manner as described with respect to FIG. 4A, and let a line, which contains the second diagonal joining the other pair of opposing points PY and PY', be represented by $LY_0$. Further, let an intersecting point of the lines $LX_0$ and $LY_0$ be represented by O.

Let a plurality m of lines, which extend in the plane containing the surface of the specimen 2 and in parallel to the line $LX_0$ and which are sequentially arranged at equal intervals e in a direction perpendicular to the line $LX_0$ on the side of the point PY with respect thereto over a range which is equal to one half of the width f smaller than the length NY of the abovesaid second diagonal, that is, equal to f/2, be represented by $LX_1$, $LX_2'$ ... $LX_{m'}$ respectively, as shown in FIG. 11 and in the same manner as described previously in respect of 4A. Let a plurality m of lines, which are sequentially arranged in parallel to the line $LX_0$ and at equal intervals e in the direction perpendicular to the line $LX_0$ on the side of the point PY' with respect thereto over the range equal to the abovesaid width f/2, be represented by $LX_1'$, $LX_2'$, ... $LX_{m'}$, respectively, in the same manner as described previously with respect to FIG. 4A.

Let a line, which passes through the point PY of the impression 3 of the specimen 2 on the specimen table 1 perpendicularly to the line $LY_0$ in the plane containing the surface of the specimen 2, be represented by $LXU_0$, and let a line, which passes through the point PY' perpendicularly to the line $LY_0$, be represented by $LXD_0$.

Let a plurality p of lines, which extend in parallel to the line $LXU_0$ and which are sequentially arranged side by side at the aforesaid equal intervals e on the side of the point PY' with respect to the line $LXU_0$ over a range of a width h1 smaller than the length of the second diagonal, be represented by $LXU_1'$, $LXU_2'$, ... $LXU_p'$, respectively, as shown in FIG. 4A. Further, let a plurality q of line, which extend in parallel to the line $LXU_0$ and which are sequentially arranged side by side at the aforesaid equal intervals e on the opposite side from the point PY' with respect to the line $LXU_0$ over a range of a width h2 equal to or smaller than the abovesaid width h1, be represented by $LXU_1$, $LXU_2$, ... $LXU_q$, respectively, as shown in FIG. 4A.

Let a plurality p of lines, which extend in parallel to the line $LXD_0$ and which are sequentially arranged side by side at the aforesaid equal intervals e on the side of the point PY with respect to the line $LXD_0$ over the range of the abovesaid width h1, be represented by $LXD_1$, $LXD_2'$, ... $LXD_p'$, respectively, as shown in FIG. 4A. Further, let a plurality q of lines, which extend in parallel to the line $LXD_0$ and which are sequentially arranged side by side at the aforesaid equal intervals e on the opposite side from the point PY with respect to the line $LXD_0$ over the range of the abovesaid width h2, be represented by $LXD_1'$, $LXD_2'$, ... $LXD_q$, respectively, as shown in FIG. 4A.

Now let it be assumed that the specimen 2 is preadjusted in position on the specimen table 1 so that the abovementioned line $LX_0$ on the specimen 2 placed on the specimen table 1 is parallel to and substantially in agreement with the line of arrangement c—c of the solid-state image sensors $E_n'$ to $E_1'$, $E_0$ and $E_1$ to $E_n$ of the one-dimensional scanning image sensing device 21, as viewed from the direction along the axis a of the holder 23 and consequently from the direction along the axis d of the tubular member 41, in the same manner as described previously with respect to the electrical system of the first embodiment of the present invention.

Further, let it be assumed that the specimen table 1 lies at its lowered reference position, as described previously in connection with the electrical system of the first embodiment of the present invention.

In such a case, the one-dimensional scanning image sensing device 21 provides the outputs $S_n'$ to $S_1'$, $S_0$ and $S_1$ to $S_n$ in the same manner as described previously with regard to FIG. 4C. The image output S, which is obtained from the one-dimensional scanning image sensing device 21 in the sequential order $S_n'$ to $S_1'$, $S_0$ and $S_1$ to $S_n$ for each scanning, is provided to the arithmetic processing circuit 51 as in the case of the first embodiment of the presenet invention.

Now, the outputs $S_n'$ to $S_1'$, $S_0$ and $S_1$ to $S_n$ which are seqentially obtained from the one-dimensional scanning image sensing device 21 by u scanning operations starting from a certain time point $t_1$ will hereinafter be represented by first outputs $S_{1n}'$ to $S_{11}'$, $S_{10}$ and $S_{11}$ to $S_{1n'}$; second outputs $S_{2n}'$ to $S_{21}'$, $S_{20}$ and $S_{21}$ to $S_{2n'}$; .... and uth outputs $S_{un}'$ to $S_{u1}'$, $S_{u0}$ and $S_{u1}$ to $S_{un'}$ respectively, as described previously in connection with FIG. 6A.

Then, the arithmetic processing circuit 51 obtains from the ith (where i=1, 2, ... u) outputs $S_{in}'$ to $S_{i1}'$, $S_{i0}$ and $S_{i1}$ to $S_{in}$ difference outputs $\Delta S_{in}'$, $\Delta S_{i(n-1)}'$, ... $\Delta S_{i1}'$, $\Delta S_{i1}$, $\Delta S_{i2}'$ ... $\Delta S_{in}$ which are the same as in the case of the first embodiment of the present invention, and the arithmetic processing circuit 51 decides and stores a maximum one of the difference outputs $\Delta S_{in'}$ to $\Delta S_{i1}'$ and $\Delta S_{i1}$ to $\Delta S_{in}$ (which maximum difference output will hereinafter be identified by $\Delta S_i$) and outputs a positive pulse $P_i$ in the same manner as described in respect of FIG. 6B.

In this way, positive pulses $P_{1'} P_{2'} \ldots P_u$ are sequentially provided from the arithmetic processing circuit 51, as is the case with the first embodiment of the present invention.

These positive pulses $P_{1'} P_{2'} \ldots P_u$ are supplied via a motor drive circuit 52 to the aforementioned motor 10, as is the case with the first embodiment of the present invention. Consequently, when supplied with the positive pulses $P_{1'} P_{2'} \ldots P_u$ one after another, the motor 10 rotates in the forward direction step by step, causing the specimen table 1 to move up from the aforementioned reference position step by step.

As in the case of the first embodiment of the present invention, after generating the positive pulses $P_1$ to $P_{u'}$ the arithmetic processing circuit 51 yields u negative pulses $P_1'$ to $P_u'$ one after another, as described previously with regard to FIG. 6B.

These negative pulses $P_1'$ to $P_u'$ are provided via the motor drive circuit 52 to the motor 10, as in the case of the first embodiment of the present invention. When supplied with the negative pulses $P_1', P_2', \ldots P_u'$ in the sequential order, the motor 10 rotates in the reverse direction step by step. In consequence, the specimen table 1 moves down from the abovesaid raised position step by step correspondingly, and the specimen table 1 thus returns to the reference position.

Moreover, as in the case of the first embodiment of the present invention, the arithmetic processing circuit 51 decides a maximum one $\Delta S_r$ of the aforesaid maximum difference outputs $\Delta S_1, \Delta S_2, \ldots \Delta S_u$ before completion of the sequential generation of the negative pulses $P_1'$ to $P_u'$, or after generating the pulse $P_u'$. Then, after generating the pulse $P_u'$, the arithmetic processing circuit outputs r positive pulses $P_1''$ to $P_r''$.

These positive pulses $P_1''$ to $P_u''$ are provided via the motor drive circuit 52 to the motor 10, as in the case of the first embodiment of the present invention.

Accordingly, the motor 10 rotates again in the forward direction step by step and the specimen table 1 moves up step by step correspondingly and stays at the raised position.

The position up to which the specimen table 1 is thus brought up step by step is the aforesaid in-focus position where the one-dimensional scanning image sensing device 21 scans the specimen 2 under the in-focus condition, as described previously in respect of the first embodiment of the present invention.

Therefore, after the specimen table 1 is brought to the in-focus position, the image output S of the one-dimensional scanning image sensing device 21 is obtained at a high level.

After the specimen table 1 is brought to the infocus position as described above, the arithmetic processing circuit 51 produces m negative pulses $G1_1$ to $G1_m$, as in the case of the first embodiment of the present invention. These m negative pulses $G1_1$ to $G1_m$ are provided via a motor drive circuit 53 to the motor 35. Therefore, by sequential application of the pulses $G1_{1'} G1_{2'} \ldots G1_{m'}$ the motor 35 rotates in the forward direction step by step. In response to this, the aforementioned movable board 22 moves along the line b—b towards the line $LX_m'$ on the stepwise basis.

As a result of this, the line $LX_m'$ on the specimen 2 is parallel to and substantially in agreement with the line of arrangement c—c of the solidstate image sensors $E_n'$ to $E_1'$, $E_0$ and $E_1$ to $E_n$, as in the case of the first embodiment of the present invention.

A plurality of sets of the outputs $S_n'$ to $S_1'$, $S_0$ and $S_1$ to $S_n'$ which are sequentially produced by $(2m+1)$ scanning operations from a time point $t_2$ after the line $LX_m'$ on the specimen 2 has been brought into substantial agreement with the line of arrangement c—c as described just above, will hereinafter be identified as outputs $QXL_{mn}'$ to $QXL_{m1}'$, $QXC_{m0}'$ and $QXR_{m1}'$ to $QXR_{mn}'$ by first scanning; outputs $QXL_{(m-1)n}'$ to $QXL_{(m-1)1}'$, $QXC_{(m-1)0}'$ and $QXR_{(m-1)1}'$ to $QXR_{(m-1)n}'$ by second scanning; ... outputs $QXL_{1n}'$ to $QXL_{11}'$, $QXC_{10}'$ and $QXR_{11}'$ to $QXR_{1n}'$ by mth scanning; outputs $QXL_{0n}$ to $QXL_{01}$, $QXC_{00}$ and $QXR_{01}$ to $QXR_{0n}$ by $(m+1)$th scanning; outputs $QXL_{1n}$ to $QXL_{11'} QXC_{10}$ and $QXR_{11}$ to $QXR_{1n}$ by $(m+2)$th scanning; outputs $QXL_{2n}$ to $QXL_{21'} QXC_{20}$ and $QXR_{21}$ to $QXR_{2n}$ by $(m+3)$th scanning; ... and outputs $QXL_{mn}$ to $QXL_{m1'} QXC_{m0}$ and $QXR_{m1}$ to $QXL_{mn}$ by $(2m+1)$th scanning, respectively, in the same manner as described previously with respect FIGS. 6A and 7A.

Then, as in the case of the first embodiment of the present invention, the arithmetic processing circuit 51 stores the abovesaid outputs $QXL_{jn}'$ to $QXL_{j1}'$, $QXC_{j0}'$ and $QXR_{j1}'$ to $QXR_{jn}'$ of the j'th ($j' = m, (m-1), \ldots 1$) scanning and obtains difference outputs $\Delta QXL_{jn'}$, $\Delta QXL_{j(n-1)'}, \ldots \Delta QXL_{j1}', \Delta QXR_{j1}'$ W$\Delta QXR_{j2}', \ldots \Delta QXR_{jn}'$.

Then the arithmetic processing circuit 51 arrays and stores the abovesaid difference outputs $\Delta QXL_{j1}'$ to $\Delta QXL_{jn}'$ in this order and detects the position on the array of the difference outputs where the difference output of a zero value, $\Delta QXL_j'$, appears for the first time after a plurality of difference outputs of positive values appear one after another, as viewed from the side of the difference output $\Delta QXL_{j1}'$ to the side of the difference output $QXL_{jn}'$, as in the case of the first embodiment of the present invention.

Thereafter the arithmetic processing circuit 51 store the output $WXL_j'$ which represents the array length from the position of the difference output $\Delta QXL_j'$ to the position of the difference output $\Delta QXL_{j1}'$.

Furthermore, as in the case of the first embodiment of the present invention, the arithmetic processing circuit 51 similarly detects the position on the array of the difference outputs where the difference output of a zero value, $\Delta QXR_j'$, appears for the first time after a plurality of difference outputs of positive values appear one after another, as viewed from the side of the difference output $\Delta QXR_{j1}'$ to the side of the difference output $\Delta QXR_{jn'}$. Then the arithmetic processing circuit 51 stores the output $WXR_j'$ which represents the array length from the position of the difference output $\Delta QXR_j'$ to the position of the difference output $\Delta QXR_{j1}'$.

Then, as in the case of the first embodiment of the present invention, the arithmetic processing circuit 51 obtains, from the output $WXL_j'$ and $WXR_j'$ representing the abovesaid array lengths, the output $MX_j'$ represented by $$MX_j' = WXL_j' + WXR_j'$$

and stores it. Then the arithmetic processing circuit 51 outputs the pulse $HX_j'$, as described previously in connection with FIG. 7B.

Furthermore, as in the case of the first embodiment of the present invention, the arithmetic processing circuit 51 stores the abovesaid outputs $QXL_{0n}$ to $QXL_{01}$, $QXC_{00}$ and $QXR_{01}$ to $QXR_{0n}$ of the $(m+1)$th scanning and obtains the difference outputs $\Delta QXL_{0n}$, $\Delta QXL_{0(n-1)}, \ldots \Delta QXL_{01}, \Delta QXR_{01}, \Delta QXR_{02}, \ldots \Delta QXR_{0n}$.

Then, as in the case of the first embodiment of the present invention, the arithmetic processing circuit 51 arrays and stores the abovesaid difference outputs $\Delta QXL_{01}$ to $\Delta QXL_{0n}$ in this order and detects the position on the array of the difference outputs where the difference output of a zero value, $\Delta QXK_0$, appears for the first time after a plurality of difference outputs of positive values appear one after another, as viewed from the side of the difference output $\Delta QXL_{01}$ to the side of the difference output $QXL_{0n}$.

Thereafter the arithmetic processing circuit 51 stores the output $WXL_0$ which represents the array length from the position of the difference output $\Delta QXL_0$ to the position of the difference output $\Delta QXL_{01}$.

Furthermore, as in the case of the first embodiment of the present invention, the arithmetic processing circuit 51 similarly detects the position on the array of the difference outputs where the difference output of a zero value, $\Delta QXR_0$, appears for the first time after a plurality of difference outputs of positive values appear one after another, as viewed from the side of the difference output $\Delta QXR_{01}$ to the side of the difference output $\Delta QXR_{0n}$. Then the arithmetic processing circuit 51 stores the output $WXR_0$ which represents the array length from the position of the difference output $\Delta QXR_0$ to the position of the difference output $\Delta QXR_{01}$.

Then, as in the case of the first embodiment of the present invention, the arithmetic processing circuit 51 obtains, from the outputs $WXL_0$ and $WXR_0$ representing the abovesaid array lengths, an output $MX_0$ represented by $$MX_0 = WXL_0 + WXR_0$$

and stores it. Then the arithmetic processing circuit outputs the pulse $HX_0$, as described previously in connection with FIG. 7B.

Furthermore, as in the case of the first embodiment of the present invention, the arithmetic processing circuit 51 stores the abovesaid outputs $QXL_{jn}$ to $QXL_{j1}$, $QXC_{j0}$ and $QXR_{j1}$ to $QXR_{jn}$ of the jth (j=1, 2 ... m) scanning and obtains difference outputs $\Delta QXL_{jn}$, $\Delta QXL_{j(n-1)}, \ldots \Delta QXL_{j1}, \Delta QXR_{j1}, \Delta QXR_{j2}, \ldots \Delta QXR_{jn}$.

Then the arithmetic processing circuit 51 arrays and stores the abovesaid difference outputs $\Delta QXL_{j1}$ to $\Delta QXL_{jn}$ in this order. Then, as in the case of the first embodiment of the present invention, the arithmetic processing circuit 51 detects the position on the array of the difference outputs where the difference output of a zero value, appears for the first time after a plurality of difference outputs of positive values appear one after another, as viewed from the side of the difference output $\Delta QXL_{j1}$ to the side of the difference output $QXL_{jn}$.

Thereafter the arithmetic processing circuit 51 stores the output $WXL_j$ which represents the array length from the position of the difference output $\Delta QXL_j$ to the position of the difference output $\Delta QXL_{j1}$.

Furthermore, as in the case of the first embodiment of the present invention, the arithmetic processing circuit 51 similarly detects the position on the array of the difference outputs where the difference output of a zero value, $\Delta QXR_j$, appears for the first time after a plurality of difference outputs of positive values appear one after another, as viewed from the side of the difference output $\Delta QXR_{j1}$ to the side of the difference output $\Delta QXR_{jn}$. Then the arithmetic processing circuit 51 stores the output $WXR_j$ which represents the array length from the position of the difference output $\Delta QXR_j$ to the position of the difference output $\Delta QXR_{j1}$.

Then, as in the case of the first embodiment of the present invention, the arithmetic processing circuit 51 obtains, from the outputs $WXL_j$ and $WXR_j$ representing the abovesaid array lengths, the output $MX_j$ represented by $$MX_j = WXL_j + WXR_j$$

and stores it. Then the arithmetic processing circuit 51 outputs the positive pulse $HX_j$, as described previously in respect of FIG. 7B.

In the manner described above, the arithmetic processing circuit 51 provides the positive pulses $HX_m'$, $HX_{(m-1)}', \ldots HX_1', HX_0, HX_1, HX_2, \ldots HX_m$ one after another, as in the case of the first embodiment of the present invention.

These pulses $HX_m', HX_{(m-1)}', \ldots HX_1', HX_0', HX_1, HX_2, \ldots HX_m$ are applied via the motor drive circuit 53 to motor 35. Supplied with the pulses $HX_m', HX_{(m-1)}', \ldots HX_1', HX_0', HX_1, HX_2, \ldots HX_m$ one after another, the motor 35 rotates in the forward direction step by step. Consequently, the movable board 22 moves along the aforementioned line b—b step by step, the distance of movement for each step being equal to the aforesaid interval.

By such step-by-step movement of the movable board 22, the aforesaid line c—c held so far at the position relative to the holder 23 where the line is substantially in agreement with the line $LX_m'$ is brought into substantial agreement with the lines $LX_{(m-1)}, LX_{(m-2)}', \ldots LX_1', LX_0', LX_1, \ldots LX_m$ one after another, as in the case of the first embodiment of the present invention.

Accordingly, the output $WXL_j'$ of the output $MX_j'$ represents the length from the central position O of the impression 3 of the specimen 2 to the marginal edge thereof on the side of the point PX' on the aforementioned line $LX_j'$, as described previously in connection with the first embodiment of the present invention. Further, the output $WXR_j'$ of the output $MX_j'$ represents the length of the impression 3 of the specimen 2 from the central position O of the impression 3 to its marginal edge on the side of the point PX on the line $LX_j'$. Accordingly, the output $MX_j'$ represents the length of the impression 3 on the line $LX_j'$.

Furthermore, the outputs $MX_0$ and $MX_j$ represents the lengths of the impression 3 on the lines $LX_0$ and $LX_j$, respectively.

Moreover, after generating the pulses $HX_m'$, $HX_{(m-1)}' \ldots HX_1', HX_0, HX_1, HX_2, \ldots HX_m$, the arithmetic processing circuit 51 produces g positive pulses $G2_1, G2_2, \ldots G2_g$ are after another.

These pulses $G2_1, G2_2, \ldots G2_g$ are provided via the motor drive circuit 53 to the motor 35.

By sequential application of the pulses $G2_{1'} G2_{2'} \ldots G2_g$, the motor 35 rotates in the forward direction step by step. In response to this, the aforementioned movable board 22 moves step by step along the line b—b towards the line $LXU_p'$ from the position relative to the holder 23 where the aforesaid line c—c is substantially in agreement with the line $LX_m$. In this case, let it be assumed that the distance between the lines $LX_m$ and $LXU_p'$ is g times larger than the aforementioned spacing e.

Accordingly, when the motor 35 is stopped from the forward step-by-step rotation and the movable board 22 is correspondingly stopped from the step-by-step movement, the movable board 22 assumes such a position relative to the holder 23 that line $LXU_p'$ on the specimen 2 is substantially in agreement with the line of arrangement c—c of the solid-state image sensors $E_n'$ to $E_1'$, $E_0$ and $E_1$ to $E_n$ of the one-dimensional scanning image sensing device 21.

Figure 13:
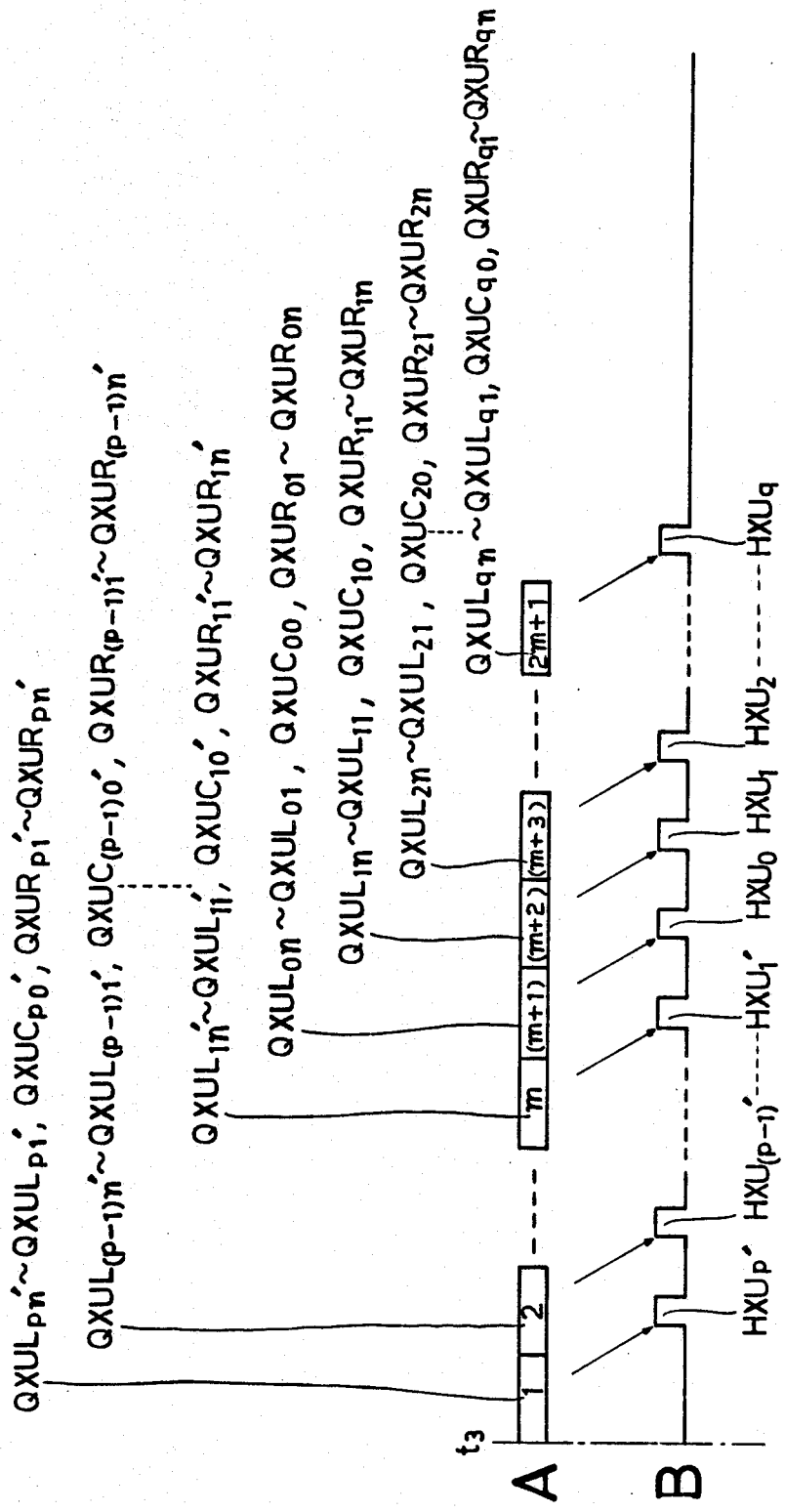
FIGS. 13 and 14 are signal arrangement diagrams explanatory of the electrical system shown in FIG. 12.

A plurality of sets of the outputs $S_n'$ to $S_1'$, $S_0$ and $S_1$ to $S_n'$ which are sequentially produced by $(p+q+1)$ scanning operations from a time point $t_4$ after the line of arrangement c—c has been brought into substantial agreement with the line $LXU_p'$ on the specimen 2 as described just above, will hereinafter be identified as outputs $QXUL_{pn}'$ to $QXUL_{p1}'$, $QXUC_{p0}'$ and $QXUR_{p1}'$ to $QXUR_{pn}'$ by first scanning; outputs $QXUL_{(p-1)n}'$ to $QXUL_{(p-1)1}'$, $QXUC_{(p-1)0}'$ and $QXUR_{(p-1)1}'$ to $QXUR_{(p-1)n}'$ by second scanning; ... outputs $QXUL_{1n}'$ to $QXUL_{11}'$, $QXUC_{10}'$ and $QXUR_{11}'$ to $QXUR_{1n}'$ by pth scanning; outputs $QXUL_{0n}$ to $QXUL_{01}$, $QXUC_{00}$ and $QXUR_{01}$ to $QXR_{0n}$ by $(p+1)$th scanning; outputs $QXUL_{1n}$ to $QXUL_{11}$, $QXUC_{10}$ and $QXUR_{11}$ to $QXUR_{1n}$ by $(p+2)$th scanning; outputs $QXUL_{2n}$ to $QXUL_{21}$, $QXUC_{20}$ and $QXUR_{21}$ to $QXUR_{2n}$ by $(p+3)$th scanning, ... and outputs $QXUL_{qn}$ to $QXUL_{q1}$, $QXUC_{q0}$ and $QXUR_{q1}$ to $QXUR_{qn}$ by $(p+q+1)$th scanning, respectively, in the same manner as described previously with respect FIG. 8A, as shown in FIG. 13A.

Then the arithmetic processing circuit 51 stores the abovesaid outputs $QXUL_{kn}'$ to $QXUL_{k1}'$, $QXUC_{k0}'$ and $QXUR_{k1}'$ to $QXUR_{kn}'$ of the k'th ($k'=p, (p-1), \ldots 2, 1$) scanning and obtains difference outputs $\Delta QXUL_{kn}'$, $\Delta QXUL_{k(n-1)}'$, ... $\Delta QXUL_{k1}'$, $\Delta QXUR_{k1}'$, $\Delta QXUR_{k2}'$, ... $\Delta QXUR_{kn}'$ which are respectively represented by $$\Delta QXUL_{kn}' = QXUL_{kn}' - QXUL_{k(n-1)}'$$

$$\Delta QXUL_{k(n-1)}' = QXUL_{k(n-1)}' - QXUL_{k(n-2)}'$$

.

.

.

$$\Delta QXUL_{k1}' = QXUL_{k1}' - QXUC_{k0}'$$

$$\Delta QXUR_{k1}' = QXUR_{k1}' - QXUC_{k0}'$$

$$\Delta QXUR_{k2}' = QXUR_{k2}' - QXUR_{k1}'$$

.

.

.

$$\Delta QXUR_{kn}' = QXUR_{kn}' - QXUR_{k(n-1)}'$$

Then the arithmetic processing circuit 51 arrays and stores the abovesaid difference outputs $\Delta QXUL_{k1}'$ to $\Delta QXUL_{kn}'$ in this order.

Then the arithmetic processing circuit 51 detects the position on the array of the difference outputs where a difference output of a zero value appears for the first time after a plurality of difference outputs of positive values appear one after another (which output will hereinafter be identified as $\Delta QXUL_m'$), as viewed from the side of the difference output $\Delta QXUL_{k1}'$ to the side of the difference output $QXUL_{kn}'$.

Thereafter the arithmetic processing circuit 51 stores an output which represents the array length from the position of the difference output $\Delta QXUL_m'$ to the position of the difference output $\Delta QXUL_{m1}'$ (which output will hereinafter be identified as $WXUL_m'$).

Furthermore, the arithmetic processing circuit 51 similarly detects the position on the array of the difference outputs where a difference output of a zero value appears for the first time after a plurality of difference outputs of positive values appear one after another (which output will hereinafter be identified as $\Delta QXUR_k'$), as viewed from the side of the difference output $\Delta QXUR_{k1}'$ to the side of the difference output $\Delta QXUR_{kn}'$.

Then the arithmetic processing circuit 51 stores an output which represents the array length from the position of the difference output $\Delta QXUR_k'$ to the position of the difference output $\Delta QXUR_{k1}'$ (which output will hereinafter be identified as $WXUR_k'$).

Then the arithmetic processing circuit 51 obtains, from the output $WXUL_k'$ and $WXUR_k'$ representing the abovesaid array lengths, an output $MXU_k'$ represented by $$MX_k' = WXUL_k' + WXUR_k'$$

and stores it.

Then the arithmetic processing circuit 51 outputs a pulse $HXU_k'$, as shown in FIG. 13B.

Furthermore the arithmetic processing circuit 51 stores the abovesaid outputs $QXUL_{0n}$ to $QXUL_{01}$, $QXUC_{00}$ and $QXUR_{01}$ to $QXUR_{0n}$ of the $(p+1)$th scanning and obtains difference outputs $\Delta QXUL_{0n}$, $\Delta QXUL_{0(n-1)}$, ... $\Delta QXUL_{01}$, $\Delta QXUR_{01}$, $\Delta QXUR_{02}$, ... $\Delta QXUR_{0n}$ which are respectively represented by $$\Delta QXUL_{0n} = QXUL_{0n} - QXUL_{0(n-1)}$$

$$\Delta QXUL_{0(n-1)} = QXUL_{0(n-1)} - QXUL_{0(n-2)}$$

.

.

.

$$\Delta QXUL_{01} = QXUL_{01} - QXUC_{00}$$

$$\Delta QXUR_{01} = QXUR_{01} - QXUC_{00}$$

$$\Delta QXUR_{02} = QXUR_{02} - QXUR_{01}$$

.

.

.

$$\Delta QXUR_{0n} = QXUR_{0n} - QXUR_{0(n-1)}$$

Then the arithmetic processing circuit 51 arrays and stores the abovesaid difference outputs $\Delta QXUL_{01}$ to $\Delta QXUL_{0n}$ in this order.

Then the arithmetic processing circuit 51 detects the position on the array of the difference outputs where a difference output of a zero value appears for the first time after a plurality of difference outputs of positive values appear one after another (which output will hereinafter be identified as $\Delta QXUL_0$), as viewed from the side of the difference output $\Delta QXUL_{01}$ to the side of the difference output $QXUL_{0n}$.

Thereafter the arithmetic processing circuit 51 stores an output which represents the array length from the position of the difference output $\Delta QXUL_0$ to the position of the difference output $\Delta QXUL_{01}$ (which output will hereinfter be identified as $WXUL_0$).

Furthermore, the arithmetic processing circuit 51 similarly detects the position on the array of the difference outputs where a difference output of a zero value appears for the first time after a plurality of difference outputs of positive values appear one after another (which output will hereinafter be identified as $\Delta QXUR_0$), as viewed from the side of the difference output $\Delta QXUR_{01}$ to the side of the difference output $\Delta QXUR_{0n}$.

Then the arithmetic processing circuit 51 stores an output which represents the array length from the position of the difference output $\Delta QXUR_0$ to the position of the difference output $\Delta QXUR_{01}$ (which output will hereinafter be identified as $WXUR_0$).

Then the arithmetic processing circuit 51 obtains, from the outputs $WXUL_0$ and $WXUR_0$ representing the abovesaid array lengths, an output $MXU_0$ represented by $$MXU_0 = WXUL_0 + WXUR_0$$

and stores it. Then the arithmetic processing circuit 51 outputs a pulse $HXU_0$, as shown in FIG. 13B.

Furthermore the arithmetic processing circuit 51 stores the abovesaid outputs $QXUL_{kn}$ to $QXUL_{k1}$, $QXUC_{k0}$ and $QXUR_{k1}$ to $QXUR_{kn}$ of the kth (k=1, 2, . . . q) scanning and obtains difference outputs $\Delta QXUL_{kn}$, $\Delta QXUL_{k(n-1)}$, . . . $\Delta QXUL_{k1}$, $\Delta QXUR_{k1}$, $\Delta QXUR_{k2}$, . . . $\Delta QXUR_{kn}$ which are respectively represented by $$\Delta QXUL_{kn} = QXUL_{kn} - QXUL_{k(n-1)}$$

$$\Delta QXUL_{k(n-1)} = QXUL_{k(n-1)} - QXUL_{k(n-2)}$$

.

.

.

$$\Delta QXUL_{k1} = QXUL_{k1} - QXUC_{k0}$$

$$\Delta QXUR_{k1} = QXUR_{k1} - QXUC_{k0}$$

$$\Delta QXUR_{k2} = QXUR_{k2} - QXUR_{k1}$$

.

.

.

$$\Delta QXUR_{kn} = QXUR_{kn} - QXUR_{k(n-1)}$$

Then the arithmetic processing circuit 51 arrays and stores the abovesaid difference outputs $\Delta QXUL_{k1}$ to $\Delta QXUL_{kn}$ in this order.

Then the arithmetic processing circuit 51 detects the position on the array of the difference outputs where a difference output of a zero value appears for the first time after a plurality of difference outputs of positive values appear one after another (which output will hereinafter be identified as $\Delta QXUL_k$), as viewed from the side of the difference output $\Delta QXUL_{k1}$ to the side of the difference output $QXUL_{kn}$.

Thereafter the arithmetic processing circuit 51 stores an output which represents the array length from the position of the difference output $\Delta QXUL_k$ to the position of the difference output $\Delta QXUL_{k1}$ (which output will hereinfter be identified as $WXUL_k$).

Furthermore, the arithmetic processing circuit 51 similarly detects the position on the array of the difference outputs where a difference output of a zero value appears for the first time after a plurality of difference outputs of positive values appear one after another (which output will hereinafter be identified as $\Delta QXUR_k$), as viewed from the side of the difference output $\Delta QXUR_{k1}$ to the side of the difference output $\Delta QXUR_{kn}$.

Then the arithmetic processing circuit 51 stores an output which represents the array length from the position of the difference output $\Delta QXUR_k$ to the position of the difference output $\Delta QXUR_{k1}$ (which output will hereinafter be identified as $WXUR_k$).

Then the arithmetic processing circuit 51 obtains, from the outputs $WXUL_k$ and $WXUR_k$ representing the abovesaid array lengths, an output $MXU_k$ represented by $$MXU_k = WXUL_k + WXUR_k$$

and stores it. Then the arithmetic processing circuit 51 outputs a pulse $HXU_k$, as shown in FIG. 13B.

In the manner described above, the arithmetic processing circuit 51 provides pulses $HXU_p'$, $HXU_{(p-1)}'$, . . . $HXU_1'$, $HXU_0$, $HXU_1$, $HXU_2$, . . . $HXU_q$ one after another.

These pulses $HXU_p'$, $HXU_{(p-1)}'$, . . . $HXU_1'$, $HXU_0'$, $HXU_1$, $HXU_2$, . . . $HXU_q$ are applied via the motor drive circuit 53 to motor 35.

Supplied with the pulses $HXU_p'$, $HXU_{(p-1)}'$, . . . $HXU_1'$, $HXU_0$, $HXU_1$, $HXU_2$, . . . $HXU_q$ one after another, the motor 35 rotates in the forward direction step by step. Consequently, the movable board 22 moves along the aforementioned line b—b step by step to the side opposite from the line $LX_m$ from such a position relative to the holder 23 that the aforesaid line c—c is substantially in agreement with the line $LXU_p'$.

By such step-by-step movement of the movable board 22, the aforesaid line c—c held so far at the position relative to the holder 23 where the line is substantially in agreement with the line $LXU_p'$ is brought into substantial agreement with the lines $LXU_{(p-1)}$, $LXU_{(p-2)}'$, . . . $LXU_1'$, $LXU_0$, $LXU_1$, . . . $LXU_q$ one after another.

Accordingly, the output $MXUL_k'$ of the output $MXU_k'$ represents the length from the central position O of the impression 3 of the specimen 2 to the marginal edge thereof on the side of the point PX' on the aforementioned line $LXD_{k'}$.

The reason is as follows: The output $WXUL_k'$ is representative of the array length from the position of the aforesaid difference output $\Delta QXUL_{k1}'$ to the position of the difference output $\Delta QXUL_{k'}'$. On the other hand, the difference output $\Delta QXUL_{k1}'$ is the difference output of a zero value that appears for the first time on the array after a plurality of difference outputs of positive values appear one after another, as viewed from the side of the difference output $\Delta QXUL_{k1}'$ to the side of the difference output $\Delta QXUL_{kn}'$. Accordingly, the position of the difference output $\Delta QXUL_k'$ on the array corresponds to the marginal edge of the impression 3 on the line $LXU_k'$ on the side of the point PX', as will be evident from the description given previously of the general outputs $S_n'$, $S_{(n-1)}'$, ... $S_1'$, $S_0$, $S_1$, $S_2$, ... $S_{(n-1)}$, $S_n$ with reference to FIGS. 4C and D.

For the same reason as mentioned above, the output $WXUR_k'$ of the output $MXU_k'$ represents the length of the impression 3 of the specimen 2 on the line $LXU_k'$ from the central position of the impression 3 to its marginal edge on the side of the point PX on the line $LXU_k'$.

Accordingly, the output $MXU_k'$ represents the length of the impression 3 on the line $LXU_k'$.

Furthermore, for the same reason as given above, the outputs $MXU_0$ and $MXU_k$ represents the lengths of the impression 3 on the lines $LXU_0$ and $LXU_k$, respectively. In this case, however, since the lines $LXU_0$ and $LXU_k$ do not extend across the empression 3, the outputs $MXU_0$ and $MXL_k$ are obtained as zero.

Moreover, after generating the pulses $HXU_p'$, $HXU_{(p-1)}'$... $HXU_1'$, $HXU_0$, $HXU_1$, $HXU_2$, ... $HXU_q$, the arithmetic processing circuit 51 yields z negative pulses $G3_1$, $G3_2$, ... $G3_z$ one another, which are provided via the motor drive circuit 53 to the motor 35.

By sequential application of the pulses $G3_1'$ $G3_2'$... $G3_z'$ the motor 35 rotates in the reverse direction step by step. In response to this, the aforementioned movable board 22 moves step by step along the line b—b towards the line $LXD_p'$ from the position relative to the holder 23 where the aforesaid line c—c is substantially in agreement with the line $LXU_q$. In this case, let it be assumed that the distance between the lines $LU_p$ and $LXD_p$ is z (where z is number of pulses $G3_1$ to $G3_z$) times larger than the aforesaid spacing e.

Accordingly, when the motor 35 stopped from the reverse step-by-step rotation and the movable pg,77 board 22 is correspondingly stopped from the step-by-step movement, the movable board 22 assumes such a position relative to the holder 23 that line $LXD_p$ on the specimen 2 is substantially in agreement with the line of arrangement c—c of the solid-state image sensors $E_n'$ to $E_1'$, $E_0$ and $E_1$ to $E_n$.

Figure 14:
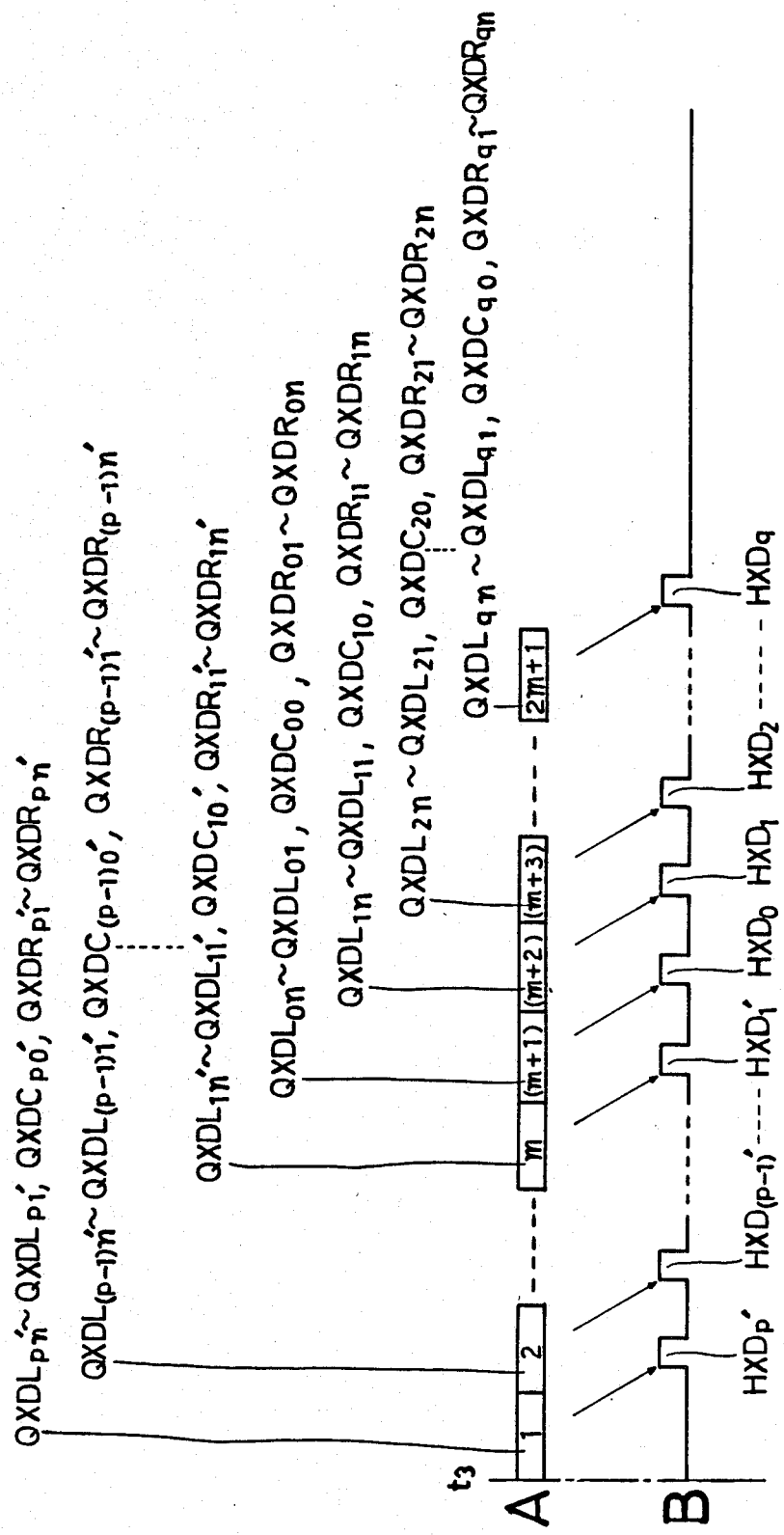

A plurally of sets of the outputs $S_n'$ to $S_1'$, $S_0$ and $S_1$ to $S_n'$ which are sequentially produced by (p+q+1) scanning operations from a time point $t_5$ after the line of arrangement c—c has been brought into substantial agreement with the line $LXD_p'$ on the specimen 2 as described just above, will hereinafter be identified as outputs $QXDL_{pn}'$ to $QXDL_{p1}'$, $QXDC_{p0}'$ and $QXDR_{p1}'$ to $QXDR_{pn}'$ by first scanning; outputs $QXDL_{(p-1)n}'$ to $QXDL_{(p-1)1}'$, $QXDC_{(p-1)0}'$ and $QXDR_{(p-1)1}'$ to $QXDR_{(p-1)n}'$ by second scanning; ... outputs $QXDL_{1n}'$ to $QXDL_{11}'$, $QXDC_{10}'$ and $QXDR_{11}'$ to $QXDR_{1n}'$ by pth scanning; outputs $QXDL_{0n}$ to $QXDL_{01}$, $QXDC_{00}$ and $QXDR_{01}$ to $QXDR_{0n}$ by (p+1)th scanning; outputs $QXDL_{1n}$ to $QXDL_{11}'$ $QXDC_{10}$ and $QXDR_{11}$ to $QXDR_{1n}$ by (p+2)th scanning; outputs $QXDL_{2n}$ to $QXDL_{21}'$ $QXDC_{20}$ and $QXDR_{21}$ to $QXDR_{2n}$ by (p+3)th scanning; ... and outputs $QXDL_{qn}$ to $QXDL_{q1}'$ $QXDC_{q0}$ and $QXDR_{q1}$ to $QXDL_{qn}$ by (p+q+1)th scanning, respectively, in the same manner as described previously with respect FIG. 13A, as shown in FIG. 14A.

Then the arithmetic processing circuit 51 stores the abovesaid outputs $QXDL_{kn}'$ to $QXDL_{k1}'$, $QXdC_{k0}'$ and $QXDR_{k1}'$ to $QXdR_{kn}'$ of the k'th (k'=p, (p−1), ... 1) scanning and obtains difference outputs $\Delta QXDL_{kn}'$, $\Delta QXDL_{k(n-1)}'$, ... $\Delta QXDL_{k1}'$, $\Delta QXDR_{k1}'$, $\Delta QXDR_{k2}'$, ... $\Delta QXDR_{kn}'$ which are respectively represented by $$\Delta QXDL_{kn}' = QXDL_{kn}' - QXDL_{k(n-1)}'$$

$$\Delta QXDL_{k(n-1)}' = QXDL_{k(n-1)}' - QXDL_{k(n-2)}'$$

$$\Delta QXDL_{k1}' = QXDL_{k1}' - QXDC_{k0}'$$

$$\Delta QXDR_{k1}' = QXDR_{k1}' - QXDC_{k0}'$$

$$\Delta QXDR_{k2}' = QXDR_{k2}' - QXDR_{k1}'$$

$$\Delta QXDR_{kn}' = QXDR_{kn}' - QXDR_{k(n-1)}'$$

Then the arithmetic processing circuit 51 arrays and stores the abovesaid difference outputs $\Delta QXDL_{k1}'$ to $\Delta QXDL_{kn}'$ in this order.

Then the arithmetic processing circuit 51 detects the position on the array of the difference outputs where a difference output of a zero value appears for the first time after a plurality of difference outputs of positive values appear one after another (which output will hereinafter be identified as $\Delta QXDL_m'$), as viewed from the side of the difference output $\Delta QXDL_{k1}'$ to the side of the difference output $QXDL_{kn}'$ Thereafter the arithmetic processing circuit 51 stores an output which represents the array length from the position of the difference output $\Delta QXDL_m'$ to the position of the difference output $\Delta QXDL_{m1}'$ (which output will hereinfter be identified as $WXDL_m'$).

Furthermore, the arithmetic processing circuit 51 similarly detects the position on the array of the difference outputs where a difference output of a zero value appears for the first time after a plurality of difference outputs of positive values appear one after another (which output will hereinafter be identified as $\Delta QXDR_k'$), viewed from the side of the difference output $\Delta QXDR_{k1}'$ to the side of the difference output $\Delta QXDR_{kn}'$.

Then the arithmetic processing circuit 51 stores an output which represents the array length from the position of the difference output $\Delta QXDR_k'$ to the position of the difference output $\Delta QXDR_{k1}'$ (which output will hereinafter be identified as $WXDR_k'$).

Then the arithmetic processing circuit 51 obtains, from the outputs $WXDL_k'$ and $WXDR_k'$ representing the abovesaid array lengths, an output $MX_k'$ represented by $$MXk_k' = WXDL_{k'} + WXDR_{k'}$$

and stores it.

Then the arithmetic processing circuit 51 outputs a pulse $HXD_k'$, as shown in FIG. 14B.

Furthermore the arithmetic processing circuit 51 stores the abovesaid outputs $QXDL_{0n}$ to $QXDL_{01}$, $QXDC_{00}$ and $QXDR_{01}$ to $QXDR_{0n}$ of the (p+1)th scanning and obtains difference outputs $\Delta QXDL_{0n}$, $\Delta QXDL_{0(n-1)}$, ... $\Delta QXDL_{01}$, $\Delta QXDR_{01}$, $W\Delta QXDR_{02}$, ... $\Delta QXDR_{0n}$ which are respectively represented by $$\Delta QXDL_{0n} = QXDL_{0n} - QXDL_{0(n-1)}$$

$$\Delta QXDL_{0(n-1)} = QXDL_{0(n-1)} - QXDL_{0(n-2)}$$

.
.
.

$$\Delta QXDL_{01} = QXDL_{01} - QXDC_{00}$$

$$\Delta QXDR_{01} = QXDR_{01} - QXDC_{00}$$

$$\Delta QXDR_{02} = QXDR_{02} - QXDR_{01}$$

.
.
.

$$\Delta QXDR_{0n} = QXDR_{0n} - QXDR_{0(n-1)}$$

Then the arithmetic processing circuit 51 arrays and stores the abovesaid difference outputs $\Delta QXDL_{01}$ to $\Delta QXDL_{0n}$ in this order.

Then the arithmetic processing circuit 51 detects the position on the array of the difference outputs where a difference output of a zero value appears for the first time after a plurality of difference outputs of positive values appear one after another (which output will hereinafter be identified as $\Delta QXDL_0$), as viewed from the side of the difference output $\Delta QXDL_{01}$ to the side of the difference output $QXDL_{0n}$.

Thereafter the arithmetic processing circuit 51 stores an output which represents the array length from the position of the difference output $\Delta QXDL_0$ to the position of the difference output $\Delta QXDL_{01}$ (which output will hereinfter be identified as $WXDL_0$).

Furthermore, the arithmetic processing circuit 51 similarly detects the position on the array of the difference outputs where a difference output of a zero value appears for the first time after a plurality of difference outputs of positive values appear one after another (which output will hereinafter be. identified as $\Delta QXDR_0$), as viewed from the side of the difference output $\Delta QXDR_{01}$ to the side of the difference output $\Delta QXDR_{0n}$.

Then the arithmetic processing circuit 51 stores an output which represents the array length from the position of the difference output $\Delta QXDR_0$ to the position of the difference output $\Delta QXDR_{01}$ (which output will hereinafter be identified as $WXDR_0$).

Then the arithmetic processing circuit 51 obtains, from the outputs $WXDL_0$ and $WXDR_0$ representing the abovesaid array lengths, an output $MXD_0$ represented by $MXD_0 = WXDL_0 + WXDR_0$ and stores it. Then the arithmetic processing circuit 51 outputs a pulse $HXD_0$, as shown in FIG. 14B.

Furthermore the arithmetic processing circuit 51 stores the abovesaid outputs $QXDL_{kn}$ to $QXDL_{k1}$, $QXDC_{k0}$ and $QXDR_{k1}$ to $QXDR_{kn}$ of the kth scanning and obtains difference outputs $\Delta QXDL_{kn}$, $\Delta QXDL_{k(n-1)}$, ... $\Delta QXDL_{k1}$, $\Delta QXDR_{k1}$, $W\Delta QXDR_{k2}$, ... $\Delta QXDR_{kn}$ which are respectively represented by $$\Delta QXDL_{kn} = QXDL_{kn} - QXDL_{k(n-1)}$$

$$\Delta QXDL_{k(n-1)} = QXDL_{k(n-1)} - QXDL_{k(n-2)}$$

-continued

.
.
.

$$\Delta QXDL_{k1} = QXDL_{k1} - QXDC_{k0}$$

$$\Delta QXDR_{k1} = QXDR_{k1} - QXDC_{k0}$$

$$\Delta QXDR_{k2} = QXDR_{k2} - QXDR_{k1}$$

.
.
.

$$\Delta QXDR_{kn} = QXDR_{kn} - QXDR_{k(n-1)}$$

Then the arithmetic processing circuit 51 arrays and stores the abovesaid difference outputs $\Delta QXDL_{k1}$ to $\Delta QXDL_{kn}$ in this order.

Then the arithmetic processing circuit 51 detects the position on the array of the difference outputs where a difference output of a zero value appears for the first time after a plurality of difference outputs of positive values appear one after another (which output will hereinafter be identified as $\Delta QXDL_k$), as viewed from the side of the difference output $\Delta QXDL_{k1}$ to the side of the difference output $QXDL_{kn}$.

Thereafter the arithmetic processing circuit 51 stores an output which represents the array length from the position of the difference output $\Delta QXDL_k$ to the position of the difference output $\Delta QXDL_{k1}$ (which output will hereinafter be identified as $WXDL_k$).

Furthermore, the arithmetic processing circuit 51 similarly detects the position on the array of the difference outputs where a difference output of a zero value appears for the first time after a plurality of difference outputs of positive values appear one after another (which output will hereinafter be identified as $\Delta QXDR_k$), as viewed from the side of the difference output $\Delta QXDR_{k1}$ to the side of the difference output $\Delta QXDR_{kn}$.

Then the arithmetic processing circuit 51 stores an output which represents the array length from the position of the difference output $\Delta QXDR_k$ to the position of the difference output $\Delta QXDR_{k1}$ (which output will hereinafter be identified as $WXDR_k$).

Then the arithmetic processing circuit 51 obtains, from the outputs $WXDL_k$ and $WXDR_k$ representing the abovesaid array lengths, an output $MXD_k$ represented by $$MXD_k = WXDL_k + WXDR_k$$

and stores it. Then the arithmetic processing circuit 51 outputs a pulse $HXD_k$, as shown in FIG. 14B.

In the manner described above, the arithmetic processing circuit 51 provides pulses $HXD_p'$, $HXD_{(p-1)}'$, ... $HXD_1'$, $HXD_0$, $HXD_1$, $HXD_2$, ... $HXD_q$ one after another.

These pulses $HXD_p'$, $HXD_{(p-1)}'$, ... $HXD_1'$, $HXD_0$, $HXD_1$, $HXD_2$, ... $HXD_q$ are applied via the motor drive circuit 53 to motor 35.

Supplied with the pulses $HXD_p'$, $HXD_{(p-1)}'$, ... $HXD_1'$, $HXD_0'$, $HXD_1$, $HXD_2$, ... $HXD_q$ one after another, the motor 35 rotates in the forward direction step by step. Consequently, the movable board 22 moves along the aforementioned line b—b step by step to the side opposite from the line $LX_m$ from such a position relative to the holder 23 that the aforesaid line c—c is substantially in agreement with the line $LXD_p'$. By such step-by-step movement of the movable board 22, the aforesaid line c—c held so far at the position relative to the holder 23 where the line is substantially in agreement with the line $LXD_p'$ is brought into substantial agreement with the lines $LXD_{(p-1)}$, $LXD_{(p-2)}$, ... $LXD_1$, $LXD_0$, $LXD_1'$, ... $LXD_q'$ one after another. Accordingly, the output $MXDL_k'$ of the output $MXD_k'$ represents the length from the central position O of the impression 3 of the specimen 2 to the marginal edge thereof on the side of the point PX' on the aforementioned line $LXD_k'$.

The reason is as follows: The output $WXDL_k'$ is representative of the array length from the position of the aforesaid difference output $\Delta QXDL_k'$ to the position of the difference output $\Delta QXDL_{k1}'$. On the other hand, the difference output $\Delta QXDL_k'$ is the difference output of a zero value that appears for the first time on the array after a plurality of difference outputs of positive values appear one after another, as viewed from the side of the difference output $\Delta QXDL_{k1}$, to the side of the difference output $\Delta QXDL_{kn}'$. Accordingly, the position of the difference output $\Delta QXDL_k'$ on the array corresponds to the marginal edge of the impression 3 on the line $LXD_k$ on the side of the point PX', as will be evident from the description given previously of the general outputs $S_n'$, $S_{(n-1)}'$, ... $S_1'$, $S_0$, $S_1$, $S_2$, ... $S_{(n-1)}'$, $S_n$ with reference to FIGS. 4C and D.

For the same reason as mentioned above, the output $WXdR_k'$ of the output $MXD_k'$ represents the length of the impression 3 of the specimen 2 on the line $LXD_k'$ from the central position O of the impression 3 to its marginal edge on the side of the point PX on the line $LXD_k'$.

Accordingly, the output $MXD_k'$ represents the length of the impression 3 on the line $LXD_k'$.

Furthermore, for the same reason as given above, the outputs $MXD_0$ and $MXD_k$ represents the lengths of the impression 3 on the lines $LXD_0$ and $LXD_k$, respectively. In this case, however, since the lines $LXD_0$ and $LXD_k$ do not cross the impression 3, the outputs $MXD_0$ and $MXD_k$ are zero.

The arithmetic processing circuit 51 stores the outputs $MXU_p'$ to $MXU_1$, $MXU_0$ and $MXU_1$ to $MXU_q$ and outputs $MXD_p'$ to $MXD_1'$ and $MXD_1$ to $MXD_q$, together with the aforementioned outputs $MX_m'$ to $MX_1$, $MX_0$ and $MX_1$ to $MX_m$.

As in the case of the first embodiment of the present invention, the arithmetic processing circuit 51 detects the maximum output MX among the outputs $MX_m'$ to $MX_1'$, $MX_0$ and $MX_1$ to $MX_m$ and yields the output MX. The output MX is the output $MX_0$ when the outputs $MX_m'$ to $MX_1'$, $MX_0$ and $MX_1$ to $MX_m$ are obtained as described above.

The output MX represents the length NX of the first diagonal joining the points PX and PX' of the impression 3 of the specimen 2, as will be seen from the foregoing description.

Further, as described above, the arithmetic processing circuit 51 stores the outputs $MXU_p'$, $MXU_{(p-1)}'$, ... $MXU_1'$, $MXU_0$, $MXU_1$, $MXU_2$, ... $MXU_q$ in this sequential order.

Then the arithmetic processing circuit 51 detects the position on the array of the above outputs where an output of a zero value appears for the first time after a plurality of outputs of other values appear one after another, as viewed from the side of the output $MXU_p'$ to the side of the output $MXU_q$ (which output will hereinafter be identified as MYU).

Then the arithmetic processing circuit 51 stores an output which represents the array length from the position of the output MYU to the position of the output $MXU_0$ (which output will hereinafter be identified as WYU).

Moreover, the arithmetic processing circuit 51 stores the outputs $MXD_p'$, $MXD_{(p-1)}'$, ... $MXD_1'$, $MXD_0$, $MXD_1$, $MXD_2$, ... $MXD_q$ in this sequential order, as described above. Then the arithmetic processing circuit detects the position on the array of the outputs where an output of a zero value appears for the first time after a plurality of outputs of other values one after another (which output will hereinafter be identified as MYD), as viewed from the side of the output $MXD_p'$ to the side of the output $MXD_q$.

Then the arithmetic processing circuit 51 stores an output which represents the array length from the position of the output MYD to the position of the output $MYD_0$ (which output will hereinafter be identified as WYD).

Thereafter the arithmetic processing circuit 51 obtains from the outputs WYU and WYD the output MY represented by $$MY = WYU \text{ and } WYD$$

The output MY represents the length NY of the second diagonal joining the points PY and PY' of the impression 3 of the specimen 2.

As described above, according to the second embodiment of the indentation hardness meter of the present invention, too, the lengths NX and NY of the first and second diagonals of the impression 3 made in the specimen 2 can be measured. Accordingly, the hardness of the specimen 2 can be measured from the lengths NX and NY.

Further, according to the second embodiment of the indentation hardness meter of the present invention described in the foregoing, too, the impression 3 made in the specimen 2 is imaged by one-dimensional scanning through the use of the one-dimensional image sensing device 21 and the outputs representing the lengths of the first and second diagonals of the impression 3 are obtained from the image output. Accordingly, the indentation hardness meter of the present invention has such a great feature that the image sensing device for obtaining the first and second diagonal-length signals may be a simple, small and inexpensive one-dimensional scanning image sensing device.

Moreover, the second embodiment of the indentation hardness meter of the present invention also does not involve scanning the entire area of the impression by the one-dimensional scanning image sensing device, and hence it has striking features that the first and second diagonal-length signals can be obtained at high speed and that the entire arrangement is simple.

While the present invention has been described as being applied to the indentation hardness meter of the type that makes a quadrangular pyramidal impression in the specimen, it will be evident that the present invention can be applied to an indentation hardness meter which makes a spherical impression in the specimen.

Various other modification and variations may be effected without departing from the spirits of the present invention.

We claim:

1. An indentaion hardness meter, characterized by the provision of:
   a specimen table for placing a specimen having made therein a quadrangular pyramidal (or spherical) impression;
   an image sensing device mount provided with a sliding board having mounted thereon a one-dimensional scanning image sensing device for imaging the impression of the specimen by scanning it;
   sliding board drive means for sliding the sliding board relative to the specimen table to a plurality of position where the one-dimensional scanning image sensing device scans and images, along a plurality of lines parallel to a first line representing the length of a first diagonal (or the diameter) of the impression, a region of the impression which contains the first line and has a width smaller than the length of a second line representing the length of a second diagonal (or the diameter perpendicular to the first line) of the impression; and
   length-signal generating means for generating from the image output of the one-dimensional scanning image sensing device a length signal representing the length of the first line.

2. An indentation hardness meter, characterized by the provision of:
   a specimen table for placing a specimen having made therein a quadrangular pyramidal (or spherical) impression;
   an image sensing device mount provided with a sliding board having mounted thereon a one-dimensional scanning image sensing device for imaging the impression of the specimen by scanning it and a rotary board rotatably supporting the sliding board;
   rotary board drive means for turning the rotary board relative to the specimen table between a first rotational position where the one-dimensional scanning image sensing device images the impression by scanning it along a line parallel to a first line representing the length of a first diagonal (or the diameter) of the impression and a second rotational position where the one-dimensional scanning image sensing device images the impression by scanning it along a line parallel to a second line representing the length of a second diagonal (or the diameter perpendicular to the first line) of the impression;
   sliding board drive means for sliding the sliding board relative to the specimen table to a plurality of positions where when the rotary board assumes the first rotational position, the one-dimensional scanning image sensing device scans and images, along a plurality of lines parallel to the first line, a region of the impression which contains the first line and has a width smaller than the length of the second line, and where when the rotary board assumes the second rotational position, the one-dimensional scanning image sensing device scans and images, along a plurality of lines parallel to the second line, a region of the impression which contains the second line and has a width smaller than the length of the first line; and
   length-signal generating means for generating from the image output of the one-dimensional scanning image sensing device a first length signal representing the length of the first line and a second length signal representing the length of the second line.

3. An indentation hardness meter, characterized by the provision of:
   a specimen table for placing a specimen having made therein a quadrangular pyramidal (or spherical) impression;
   an image sensing device mount provided with a sliding board having mounted thereon a one-dimensional scanning image sensing device for imaging the impression of the specimen by scanning it;
   sliding board drive means for sliding the sliding board relative to the specimen table to a plurality of positions where the one-dimensional scanning image sensing device scans and images, along a plurality of lines parallel to a first line representing the length of a first diagonal (or the diameter) of the impression, a first region of the impression which contains the first line and has a width smaller than the length of a second line representing the length of a second diagonal (or the diameter perpendicular to the first line) of the impression, and a plurality of positions where the one-dimensional scanning image sensing device scans and images, along a plurality of lines parallel to the first line, a second region of the impression which contains one free end of the second line and has a width smaller than the length the second line; and
   length-signal generating means for generating from the image output of the one-dimensional scanning image sensing device a first length signal representing the length of the first line and a second length signal representing the length of the second line.

* * * * *